(12) United States Patent
Hallwirth et al.

(10) Patent No.: US 12,286,457 B2
(45) Date of Patent: Apr. 29, 2025

(54) AAV CAPSID POLYNUCLEOTIDES AND POLYPEPTIDES AND VIRIONS CONTAINING THE SAME

(71) Applicants: Children's Medical Research Institute, Westmead (AU); The Sydney Children's Hospitals Network (Randwick and Westmead) (Incorporating the Royal Alexandra Hospital for Children), Westmead (AU)

(72) Inventors: Claus Hallwirth, Parramatta (AU); Ian Alexander, Pennant Hills (AU)

(73) Assignees: Children's Medical Research Institute, Westmead (AU); The Sydney Children's Hospital Network (Randwick and Westmead) (Incorporating the Royal Alexandra Hospital for Children, Westmead (AU)

( * ) Notice: Subject to any disclaimer, the term of this patent is extended or adjusted under 35 U.S.C. 154(b) by 1156 days.

(21) Appl. No.: 17/058,383

(22) PCT Filed: May 31, 2019

(86) PCT No.: PCT/AU2019/050556
§ 371 (c)(1),
(2) Date: Nov. 24, 2020

(87) PCT Pub. No.: WO2019/227168
PCT Pub. Date: Dec. 5, 2019

(65) Prior Publication Data
US 2021/0122789 A1    Apr. 29, 2021

(30) Foreign Application Priority Data
May 31, 2018  (AU) ................................ 2018901931

(51) Int. Cl.
*C07K 14/075* (2006.01)
*C12N 15/10* (2006.01)
*C12N 15/86* (2006.01)

(52) U.S. Cl.
CPC ........ *C07K 14/075* (2013.01); *C12N 15/1068* (2013.01); *C12N 15/86* (2013.01); *C12N 2750/14121* (2013.01)

(58) Field of Classification Search
None
See application file for complete search history.

(56) References Cited

FOREIGN PATENT DOCUMENTS

WO    WO 2017/192699    11/2017

OTHER PUBLICATIONS

Bello et al., "Isolation and evaluation of novel adeno-associated virus sequences from porcine tissues," Gene Therapy (2009) 16:1320-1328.
Bello et al., "Novel Adeno-associated Viruses Derived From Pig Tissues Transduce Most Major Organs in Mice," Scientific Reports (2014) 4:6644.
Bodewes et al., "Identification of Multiple Novel Viruses, Including a Parvovirus and a Hepevirus, in Feces of Red Foxes," J Virology (2013) 87(13):7758-7764.
Carbanes-Creus et al., "Codon-Optimization of Wild-Type Adeno-Associated Virus Capsid Sequences Enhances DNA Family Shuffling while Conserving Functionality," Mol Ther: Methods & Clinical Development (2019) 12:71-84.

*Primary Examiner* — Nicole Kinsey White
(74) *Attorney, Agent, or Firm* — MORRISON & FOERSTER LLP

(57) ABSTRACT

The present disclosure relates generally to polypeptides derived from marsupial adeno-associated vims (AAV). The disclosure is also related to nucleic acid molecules encoding the polypeptides, and vectors comprising the nucleic acid molecules, and AAV vectors comprising the polypeptides. The disclosure also relates to uses of the nucleic acid molecules, polypeptides and AAV vectors, such as for capsid diversification.

10 Claims, 3 Drawing Sheets
Specification includes a Sequence Listing.

SEQUENCE LISTING

<160> NUMBER OF SEQ ID NOS: 12

<210> SEQ ID NO 1
<211> LENGTH: 3462
<212> TYPE: DNA
<213> ORGANISM: Artificial Sequence
<220> FEATURE:
<223> OTHER INFORMATION: Consensus mAAV sequence (DNA)

<400> SEQUENCE: 1

```
aaatctggag gaatatgagg agatactgct aaatattccc gccagattgc agttggcagc      60
caccgcggca gcatcgctcc cgctcccgtc ctcaggtagg agacaggcag cagagactca     120
gagcagttca ggccgtaccg ctcctttgta ttacggtaaa catacccaaa aatacatgga     180
tctcgtggcc tggttagtgg aggaaggtat cacttccgag aaacaatgga ttgtcgagaa     240
tcaggagagc tatctctcct tccaggcgac cagtaatggc gccggcagca tcaaagcggc     300
tctggacaat gccagtaaga tcatgaatct gacaaagact gccgccgatt atctgatcac     360
caaacacgag tcaaattttg acaacatcga agagaacaga atttacaaaa tatttgacat     420
gaacggatac gacccgctgt acgctggaaa tattctgaca ggatggtgca agagagaatt     480
tggcaaaaga aacactatct ggctgtatgg aaaagccacc acgggaaaga caaatatcgc     540
tgaagtcatc agccacagcg tccctttctg gggctgcgtg aactggacca acgagaactt     600
tccgttcaac gactgcgtgg acaagatgat catctggtgg gaagaaggca gatgacctc      660
caaggtagtg gagaccgcta aagctatcct gggggtgcc aaagtcagag ttgaccagaa      720
gtgtaaaagc tctgttcaac tggacagcac cccggtcatc atcaccagca cacggacat      780
gtgctacgta gtggacggca acaccacgac ctttgaacac aagcagccgt cacaggaccg     840
catgttccag ttcctgctca tgaagagact tccggacgat tttggcaagg tcacgcgaga     900
agaggtcaga cagtttttca atgggccaa tgagaataaa gttgacgtca cccgggaatt      960
taccgtcaag aaagggcgc caagcgaatc tcccgccaaa actgatgacg acagaaaacg     1020
gaagtggaac tttctaaagg ctccgcctac cgctgagcct ccgcataaaa agcgcgccac     1080
ggcgcccaaa gcgtcatttc cttttcgcga ccggacgaac gaggagatta tcgagagaga     1140
cgctcccacc caggaatctg acctcgaatt tctgaaaagg tttggacttg acttgaaaca     1200
gtcagaaaat tcagagtcaa attttaaacc tgacgagatc gaaaactgtg atctcgacga     1260
cattcaggat gagcaatgac tttgtagatg tctttttag aagcgtttga ggactggtac     1320
gaaaaagcag cggctacttg gcgacatctc gaacctggcg cccccgtcc taaagccaac      1380
cagcagcatc aggaacagca tcatccggtt cctgctgaag agcctaaaga tcaagctcga     1440
ggccttgtgc tacctggcta caagtacctc ggcccctta acggccttga taaaggtgat     1500
ccggttaatc aagcggacgc tgcggcgctt gaacacgata aagcgtacaa ccaccttctc     1560
gaagaaggac aaaacccgta cctcgtgtat aacgaggctg ataagcattt ccaggaaact     1620
ctacagggg atacgagctt cggcggtaac ctcggcaaag cagtcttcca aggcaagaaa     1680
cgagtcctag agccctttgg actcgttgac gaggagcctc acgaactggc tccacctcca     1740
aaaaagaaga caaaacagga atacaaagac actctagagg ctattcctcc tcctagcaga     1800
gaggaacaga ctcctcagaa gggatcttca gcatccaaaa acggagcctc atcttcagca     1860
gcagcagcag cccccagtaa tttgggatct ggtatcatgg cagaaggcgg tggcgcacca     1920
atgggcgaca tcaacaggg tgccgatgga gtggtaatg cctcgggaaa ttggcattgc     1980
gattcccact ggatgggcga caaagtcgtc acccgcacca ccagaacctg gtcctgccc      2040
```

| | |
|---|---|
| acctacaaca accacctcta ccaagccatc gacgagaata ctactctcgg atccgccaac | 2100 |
| aacttctacg gattcagcac cccatggggg tactttgact ttaaccgctt ccactgccac | 2160 |
| ttctccccac gtgactggca aagactcatc aacaacaact ggggcatccg acccagaagc | 2220 |
| ctcagattca agctgttcaa catccaagtc aaggaggtca cgacgacgtc gggcgaaacg | 2280 |
| accatcgcca ataaccttac cagcacggtt caggtttttg cggatgaaga aatgcacctc | 2340 |
| ccgtacgtct tagggagtgc ccacgacggg tgctttcctc catttccacc agacatttac | 2400 |
| atgctgcccc aatacgggta ctgcactctg gactatcagg gactccacca agacaggagc | 2460 |
| gccttctact gtctggagta cttcccttct cagatgctga gaacgggcaa caactttgag | 2520 |
| cttacttaca actttgagaa gctgcctttc cacagcatgt ggatgcacaa ccagtccctg | 2580 |
| gacaggatca tgaatcctct catcgatcag tacctgtatc gcttcgcctc caagactggc | 2640 |
| aacacatgga cataccaaaa aggcagcaaa gacgacaaga ccgctcaagc cagaaactgg | 2700 |
| cttcctggac cctccatcag aaatcagcct ctgtactcga gtggtaatca aaccaacctc | 2760 |
| tcgggatacg atatcgctcc aaaaacagaa gtcaacgaga acagatgac tgtgtttcct | 2820 |
| ggacttttcta tggccaccga aaacgagagg agcggaacca tcaaagagca gccaacgtcc | 2880 |
| aatctgctca tctttgccaa caaagcggat gcggctacct ctcagaccac ttctagcgtg | 2940 |
| ggcagtacag cgacactcct ggtcaccaac gaaaacgaag tcaagactgt caatccctcc | 3000 |
| gccaccgaag cgtggggttc ggctgcggcc aacaaacaga catctgctac cgcctctcaa | 3060 |
| agcgtggcta ttcacgctca aggcgtggtg ccaggcatgg tctggcaaga cagagacatc | 3120 |
| tactttcagg gccccatctg ggccaagatc ccgcatacag atggacactt tcacccatct | 3180 |
| cctctcatgg gtggattcgg actcaaacat cctcctccac aaattttcat taaaaacact | 3240 |
| cctgtccccct ccaatcctgc taccacgtac accaccgcca agtacaactc cttcatcacc | 3300 |
| cagtactcca ccggtcaagt gactgtggag attgactggg aactccagaa ggagacctcc | 3360 |
| aaaaagtgga accccgagat ccagttcacc tccaattaca acgggacaga cacgctcgga | 3420 |
| ttcgctccag atgccgctgg agactacacc gaaccacgtg cc | 3462 |

<210> SEQ ID NO 2
<211> LENGTH: 2175
<212> TYPE: DNA
<213> ORGANISM: Artificial Sequence
<220> FEATURE:
<223> OTHER INFORMATION: Consensus mAAV cap (DNA

<400> SEQUENCE: 2

| | |
|---|---|
| atgtcttttt tagaagcgtt tgaggactgg tacgaaaaag cagcggctac ttggcgacat | 60 |
| ctcgaacctg gcgcccccg tcctaaagcc aaccagcagc atcaggaaca gcatcatccg | 120 |
| gttcctgctg aagagcctaa agatcaagct cgaggccttg tgctacctgg ctacaagtac | 180 |
| ctcggcccct ttaacggcct tgataaaggt gatccggtta tcaagcgga cgctgcggcg | 240 |
| cttgaacacg ataaagcgta caaccacctt ctcgaagaag acaaaaccc gtacctcgtg | 300 |
| tataacgagg ctgataagca tttccaggaa actctacagg gggatacgag cttcggcggt | 360 |
| aacctcggca aagcagtctt ccaaggcaag aaacgagtcc tagagccctt tggactcgtt | 420 |
| gacgaggagc ctcacgaact ggctccacct ccaaaaaaga agacaaaaca ggaatacaaa | 480 |
| gacactctag aggctattcc tcctcctagc agagaggaac agactcctca gaagggatct | 540 |
| tcagcatcca aaaacggagc ctcatcttca gcagcagcag cagcccccag taatttggga | 600 |

-continued

```
tctggtatca tggcagaagg cggtggcgca ccaatgggcg acaatcaaca gggtgccgat      660
ggagtgggta atgcctcggg aaattggcat tgcgattccc actggatggg cgacaaagtc      720
gtcacccgca ccaccagaac ctgggtcctg cccacctaca caaccacct ctaccaagcc      780
atcgacgaga atactactct cggatccgcc aacaacttct acggattcag cacccccatgg     840
gggtactttg actttaaccg cttccactgc cacttctccc cacgtgactg gcaaagactc      900
atcaacaaca actggggcat ccgacccaga agcctcagat tcaagctgtt caacatccaa      960
gtcaaggagg tcacgacgac gtcgggcgaa acgaccatcg ccaataacct taccagcacg     1020
gttcaggttt ttgcggatga agaaatgcac ctcccgtacg tcttagggag tgcccacgac     1080
gggtgctttc ctccatttcc accagacatt tacatgctgc cccaatacgg gtactgcact     1140
ctggactatc agggactcac cacagacagg agcgccttct actgtctgga gtacttccct     1200
tctcagatgc tgagaacggg caacaacttt gagcttactt acaactttga gaagctgcct     1260
ttccacagca tgtggatgca caaccagtcc ctggacagga tcatgaatcc tctcatcgat     1320
cagtacctgt atcgcttcgc ctccaagact ggcaacacat ggacatacca aaaaggcagc     1380
aaagacgaca agaccgctca agccagaaac tggcttcctg gaccctccat cagaaatcag     1440
cctctgtact cgagtggtaa tcaaaccaac ctctcgggat acgatatcgc tccaaaaaca     1500
gaagtcaacg agaaacagat gactgtgttt cctggacttt ctatggccac cgaaaacgag     1560
aggagcggaa ccatcaaaga gcagccaacg tccaatctgc tcatctttgc caacaaagcg     1620
gatgcggcta cctctcagac cacttctagc gtgggcagta cagcgacact cctggtcacc     1680
aacgaaaacg aagtcaagac tgtcaatccc tccgccaccg aagcgtgggg ttcggctgcg     1740
gccaacaaac agacatctgc taccgcctct caaagcgtgg ctattcacgc tcaaggcgtg     1800
gtgccaggca tggtctggca agacagagac atctactttc agggcccat ctgggccaag     1860
atcccgcata cagatggaca ctttcaccca tctcctctca tgggtggatt cggactcaaa     1920
catcctcctc cacaaatttt cattaaaaac actcctgtcc cctccaatcc tgctaccacg     1980
tacaccaccg ccaagtacaa ctccttcatc acccagtact ccaccggtca agtgactgtg     2040
gagattgact gggaactcca gaaggagacc tccaaaaagt ggaaccccga gatccagttc     2100
acctccaatt acaacgggac agacacgctc ggattcgctc cagatgccgc tggagactac     2160
accgaaccac gtgcc                                                       2175
```

<210> SEQ ID NO 3
<211> LENGTH: 725
<212> TYPE: PRT
<213> ORGANISM: Artificial Sequence
<220> FEATURE:
<223> OTHER INFORMATION: Consensus mAAV capsid protein

<400> SEQUENCE: 3

```
Met Ser Phe Leu Glu Ala Phe Glu Asp Trp Tyr Glu Lys Ala Ala Ala
1               5                   10                  15

Thr Trp Arg His Leu Glu Pro Gly Ala Pro Arg Pro Lys Ala Asn Gln
            20                  25                  30

Gln His Gln Glu Gln His His Pro Val Pro Ala Glu Glu Pro Lys Asp
        35                  40                  45

Gln Ala Arg Gly Leu Val Leu Pro Gly Tyr Lys Tyr Leu Gly Pro Phe
    50                  55                  60

Asn Gly Leu Asp Lys Gly Asp Pro Val Asn Gln Ala Asp Ala Ala Ala
65                  70                  75                  80
```

-continued

```
Leu Glu His Asp Lys Ala Tyr Asn His Leu Glu Glu Gly Gln Asn
                 85                  90                  95

Pro Tyr Leu Val Tyr Asn Glu Ala Asp Lys His Phe Gln Glu Thr Leu
            100                 105                 110

Gln Gly Asp Thr Ser Phe Gly Gly Asn Leu Gly Lys Ala Val Phe Gln
            115                 120                 125

Gly Lys Lys Arg Val Leu Glu Pro Phe Gly Leu Val Asp Glu Glu Pro
        130                 135                 140

His Glu Leu Ala Pro Pro Lys Lys Lys Thr Lys Gln Glu Tyr Lys
145                 150                 155                 160

Asp Thr Leu Glu Ala Ile Pro Pro Ser Arg Glu Glu Gln Thr Pro
                165                 170                 175

Gln Lys Gly Ser Ser Ala Ser Lys Asn Gly Ala Ser Ser Ala Ala
            180                 185                 190

Ala Ala Ala Pro Ser Asn Leu Gly Ser Gly Ile Met Ala Glu Gly Gly
        195                 200                 205

Gly Ala Pro Met Gly Asp Asn Gln Gln Gly Ala Asp Gly Val Gly Asn
    210                 215                 220

Ala Ser Gly Asn Trp His Cys Asp Ser His Trp Met Gly Asp Lys Val
225                 230                 235                 240

Val Thr Arg Thr Thr Arg Thr Trp Val Leu Pro Thr Tyr Asn Asn His
                245                 250                 255

Leu Tyr Gln Ala Ile Asp Glu Asn Thr Thr Leu Gly Ser Ala Asn Asn
            260                 265                 270

Phe Tyr Gly Phe Ser Thr Pro Trp Gly Tyr Phe Asp Phe Asn Arg Phe
        275                 280                 285

His Cys His Phe Ser Pro Arg Asp Trp Gln Arg Leu Ile Asn Asn Asn
    290                 295                 300

Trp Gly Ile Arg Pro Arg Ser Leu Arg Phe Lys Leu Phe Asn Ile Gln
305                 310                 315                 320

Val Lys Glu Val Thr Thr Thr Ser Gly Glu Thr Thr Ile Ala Asn Asn
                325                 330                 335

Leu Thr Ser Thr Val Gln Val Phe Ala Asp Glu Glu Met His Leu Pro
            340                 345                 350

Tyr Val Leu Gly Ser Ala His Asp Gly Cys Phe Pro Pro Phe Pro Pro
        355                 360                 365

Asp Ile Tyr Met Leu Pro Gln Tyr Gly Tyr Cys Thr Leu Asp Tyr Gln
    370                 375                 380

Gly Leu Thr Thr Asp Arg Ser Ala Phe Tyr Cys Leu Glu Tyr Phe Pro
385                 390                 395                 400

Ser Gln Met Leu Arg Thr Gly Asn Asn Phe Glu Leu Thr Tyr Asn Phe
                405                 410                 415

Glu Lys Leu Pro Phe His Ser Met Trp Met His Asn Gln Ser Leu Asp
            420                 425                 430

Arg Ile Met Asn Pro Leu Ile Asp Gln Tyr Leu Tyr Arg Phe Ala Ser
        435                 440                 445

Lys Thr Gly Asn Thr Trp Thr Tyr Gln Lys Gly Ser Lys Asp Asp Lys
    450                 455                 460

Thr Ala Gln Ala Arg Asn Trp Leu Pro Gly Pro Ser Ile Arg Asn Gln
465                 470                 475                 480

Pro Leu Tyr Ser Ser Gly Asn Gln Thr Asn Leu Ser Gly Tyr Asp Ile
                485                 490                 495

Ala Pro Lys Thr Glu Val Asn Glu Lys Gln Met Thr Val Phe Pro Gly
```

```
                    500                 505                 510
Leu Ser Met Ala Thr Glu Asn Glu Arg Ser Gly Thr Ile Lys Glu Gln
                515                 520                 525
Pro Thr Ser Asn Leu Leu Ile Phe Ala Asn Lys Ala Asp Ala Ala Thr
            530                 535                 540
Ser Gln Thr Thr Ser Ser Val Gly Ser Thr Ala Thr Leu Leu Val Thr
545                 550                 555                 560
Asn Glu Asn Glu Val Lys Thr Val Asn Pro Ser Ala Thr Glu Ala Trp
                565                 570                 575
Gly Ser Ala Ala Ala Asn Lys Gln Thr Ser Thr Ala Ser Gln Ser
            580                 585                 590
Val Ala Ile His Ala Gln Gly Val Val Pro Gly Met Val Trp Gln Asp
        595                 600                 605
Arg Asp Ile Tyr Phe Gln Gly Pro Ile Trp Ala Lys Ile Pro His Thr
    610                 615                 620
Asp Gly His Phe His Pro Ser Pro Leu Met Gly Gly Phe Gly Leu Lys
625                 630                 635                 640
His Pro Pro Pro Gln Ile Phe Ile Lys Asn Thr Pro Val Pro Ser Asn
                645                 650                 655
Pro Ala Thr Thr Tyr Thr Thr Ala Lys Tyr Asn Ser Phe Ile Thr Gln
            660                 665                 670
Tyr Ser Thr Gly Gln Val Thr Val Glu Ile Asp Trp Glu Leu Gln Lys
675                 680                 685
Glu Thr Ser Lys Lys Trp Asn Pro Glu Ile Gln Phe Thr Ser Asn Tyr
    690                 695                 700
Asn Gly Thr Asp Thr Leu Gly Phe Ala Pro Asp Ala Ala Gly Asp Tyr
705                 710                 715                 720
Thr Glu Pro Arg Ala
                725

<210> SEQ ID NO 4
<211> LENGTH: 2208
<212> TYPE: DNA
<213> ORGANISM: Artificial Sequence
<220> FEATURE:
<223> OTHER INFORMATION: Consensus mAAV cap with 10 aa C terminus
      extension (DNA)

<400> SEQUENCE: 4 atgtctttt  tagaagcgtt  tgaggactgg  tacgaaaaag  cagcggctac  ttggcgacat      60
ctcgaacctg  gcgcccccg   tcctaaagcc  aaccagcagc  atcaggaaca  gcatcatccg     120
gttcctgctg  aagagcctaa  agatcaagct  cgaggccttg  tgctacctgg  ctacaagtac     180
ctcggcccct  ttaacggcct  tgataaaggt  gatccggtta  atcaagcgga  cgctgcggcg     240
cttgaacacg  ataaagcgta  caaccacctt  ctcgaagaag  acaaaaaccc  gtacctcgtg     300
tataacgagg  ctgataagca  tttccaggaa  actctacagg  gggatacgag  cttcggcggt     360
aacctcggca  aagcagtctt  ccaaggcaag  aaacgagtcc  tagagccctt  tggactcgtt     420
gacgaggagc  tcacgaact   ggctccacct  ccaaaaaaga  agacaaaaca  ggaatacaaa     480
gacactctag  aggctattcc  tcctcctagc  agagaggaac  agactcctca  gaagggatct     540
tcagcatcca  aaacggagc   ctcatcttca  gcagcagcag  cagcccccag  taatttggga     600
tctggtatca  tggcagaagg  cggtggcgca  ccaatgggcg  acaatcaaca  gggtgccgat     660
ggagtgggta  atgcctcggg  aaattggcat  tgcgattccc  actggatggg  cgacaaagtc     720
```

```
gtcacccgca ccaccagaac ctgggtcctg cccacctaca acaaccacct ctaccaagcc    780
atcgacgaga atactactct cggatccgcc aacaacttct acggattcag caccccatgg    840
gggtactttg actttaaccg cttccactgc cacttctccc acgtgactg gcaaagactc    900
atcaacaaca actggggcat ccgacccaga agcctcagat tcaagctgtt caacatccaa    960
gtcaaggagg tcacgacgac gtcgggcgaa acgaccatcg ccaataacct taccagcacg   1020
gttcaggttt ttgcggatga agaaatgcac ctcccgtacg tcttagggag tgcccacgac   1080
gggtgctttc ctccatttcc accagacatt tacatgctgc cccaatacgg gtactgcact   1140
ctggactatc agggactcac cacagacagg agcgccttct actgtctgga gtacttccct   1200
tctcagatgc tgagaacggg caacaacttt gagcttactt acaactttga agctgcct    1260
ttccacagca tgtggatgca caaccagtcc ctggacagga tcatgaatcc tctcatcgat   1320
cagtacctgt atcgcttcgc ctccaagact ggcaacacat ggacatacca aaaaggcagc   1380
aaagacgaca agaccgctca agccagaaac tggcttcctg gaccctccat cagaaatcag   1440
cctctgtact cgagtggtaa tcaaaccaac ctctcgggat acgatatcgc tccaaaaaca   1500
gaagtcaacg agaaacagat gactgtgttt cctggactt ctatggccac cgaaaacgag   1560
aggagcggaa ccatcaaaga gcagccaacg tccaatctgc tcatctttgc caacaaagcg   1620
gatgcggcta cctctcagac cacttctagc gtgggcagta cagcgacact cctggtcacc   1680
aacgaaaacg aagtcaagac tgtcaatccc tccgccaccg aagcgtgggg ttcggctgcg   1740
gccaacaaac agacatctgc taccgcctct caaagcgtgg ctattcacgc tcaaggcgtg   1800
gtgccaggca tggtctggca agacagagac atctactttc agggccccat ctgggccaag   1860
atcccgcata cagatggaca ctttcacccca tctcctctca tgggtggatt cggactcaaa   1920
catcctcctc cacaaattt cattaaaaac actcctgtcc cctccaatcc tgctaccacg   1980
tacaccaccg ccaagtacaa ctccttcatc acccagtact ccaccggtca agtgactgtg   2040
gagattgact gggaactcca gaaggagacc tccaaaaagt ggaaccccga gatccagttc    2100
acctccaatt acaacgggac agacacgctc ggattcgctc cagatgccgc tggagactac   2160
accgaaccac gtgccattgg cacccgttac ctcacccgtc ccctgtaa                2208
```

<210> SEQ ID NO 5
<211> LENGTH: 735
<212> TYPE: PRT
<213> ORGANISM: Artificial Sequence
<220> FEATURE:
<223> OTHER INFORMATION: Consensus mAAV capsid protein 10 aa C terminus extension

<400> SEQUENCE: 5

```
Met Ser Phe Leu Glu Ala Phe Glu Asp Trp Tyr Glu Lys Ala Ala Ala
1               5                   10                  15

Thr Trp Arg His Leu Glu Pro Gly Ala Pro Arg Pro Lys Ala Asn Gln
            20                  25                  30

Gln His Gln Glu Gln His His Pro Val Pro Ala Glu Pro Lys Asp
        35                  40                  45

Gln Ala Arg Gly Leu Val Leu Pro Gly Tyr Lys Tyr Leu Gly Pro Phe
    50                  55                  60

Asn Gly Leu Asp Lys Gly Asp Pro Val Asn Gln Ala Asp Ala Ala Ala
65                  70                  75                  80

Leu Glu His Asp Lys Ala Tyr Asn His Leu Leu Glu Glu Gly Gln Asn
                85                  90                  95
```

```
Pro Tyr Leu Val Tyr Asn Glu Ala Asp Lys His Phe Gln Glu Thr Leu
            100                 105                 110

Gln Gly Asp Thr Ser Phe Gly Asn Leu Gly Lys Ala Val Phe Gln
        115                 120                 125

Gly Lys Lys Arg Val Leu Glu Pro Phe Gly Leu Val Asp Glu Pro
    130                 135                 140

His Glu Leu Ala Pro Pro Lys Lys Thr Lys Gln Glu Tyr Lys
145                 150                 155                 160

Asp Thr Leu Glu Ala Ile Pro Pro Ser Arg Glu Gln Thr Pro
                165                 170                 175

Gln Lys Gly Ser Ser Ala Ser Lys Asn Gly Ala Ser Ser Ala Ala
            180                 185                 190

Ala Ala Ala Pro Ser Asn Leu Gly Ser Gly Ile Met Ala Glu Gly Gly
        195                 200                 205

Gly Ala Pro Met Gly Asp Asn Gln Gln Gly Ala Asp Gly Val Gly Asn
    210                 215                 220

Ala Ser Gly Asn Trp His Cys Asp Ser His Trp Met Gly Asp Lys Val
225                 230                 235                 240

Val Thr Arg Thr Thr Arg Thr Trp Val Leu Pro Thr Tyr Asn Asn His
                245                 250                 255

Leu Tyr Gln Ala Ile Asp Glu Asn Thr Thr Leu Gly Ser Ala Asn Asn
            260                 265                 270

Phe Tyr Gly Phe Ser Thr Pro Trp Gly Tyr Phe Asp Phe Asn Arg Phe
        275                 280                 285

His Cys His Phe Ser Pro Arg Asp Trp Gln Arg Leu Ile Asn Asn
    290                 295                 300

Trp Gly Ile Arg Pro Arg Ser Leu Arg Phe Lys Leu Phe Asn Ile Gln
305                 310                 315                 320

Val Lys Glu Val Thr Thr Ser Gly Glu Thr Thr Ile Ala Asn Asn
                325                 330                 335

Leu Thr Ser Thr Val Gln Val Phe Ala Asp Glu Glu Met His Leu Pro
            340                 345                 350

Tyr Val Leu Gly Ser Ala His Asp Gly Cys Phe Pro Pro Phe Pro Pro
        355                 360                 365

Asp Ile Tyr Met Leu Pro Gln Tyr Gly Tyr Cys Thr Leu Asp Tyr Gln
370                 375                 380

Gly Leu Thr Thr Asp Arg Ser Ala Phe Tyr Cys Leu Glu Tyr Phe Pro
385                 390                 395                 400

Ser Gln Met Leu Arg Thr Gly Asn Asn Phe Glu Leu Thr Tyr Asn Phe
                405                 410                 415

Glu Lys Leu Pro Phe His Ser Met Trp Met His Asn Gln Ser Leu Asp
            420                 425                 430

Arg Ile Met Asn Pro Leu Ile Asp Gln Tyr Leu Tyr Arg Phe Ala Ser
        435                 440                 445

Lys Thr Gly Asn Thr Trp Thr Tyr Gln Lys Gly Ser Lys Asp Asp Lys
    450                 455                 460

Thr Ala Gln Ala Arg Asn Trp Leu Pro Gly Pro Ser Ile Arg Asn Gln
465                 470                 475                 480

Pro Leu Tyr Ser Ser Gly Asn Gln Thr Asn Leu Ser Gly Tyr Asp Ile
                485                 490                 495

Ala Pro Lys Thr Glu Val Asn Glu Lys Gln Met Thr Val Phe Pro Gly
            500                 505                 510

Leu Ser Met Ala Thr Glu Asn Glu Arg Ser Gly Thr Ile Lys Glu Gln
```

-continued

```
            515                 520                 525
Pro Thr Ser Asn Leu Leu Ile Phe Ala Asn Lys Ala Asp Ala Ala Thr
            530                 535                 540
Ser Gln Thr Thr Ser Ser Val Gly Ser Thr Ala Thr Leu Leu Val Thr
545                 550                 555                 560
Asn Glu Asn Glu Val Lys Thr Val Asn Pro Ser Ala Thr Glu Ala Trp
                565                 570                 575
Gly Ser Ala Ala Ala Asn Lys Gln Thr Ser Ala Thr Ala Ser Gln Ser
            580                 585                 590
Val Ala Ile His Ala Gln Gly Val Val Pro Gly Met Val Trp Gln Asp
                595                 600                 605
Arg Asp Ile Tyr Phe Gln Gly Pro Ile Trp Ala Lys Ile Pro His Thr
            610                 615                 620
Asp Gly His Phe His Pro Ser Pro Leu Met Gly Gly Phe Gly Leu Lys
625                 630                 635                 640
His Pro Pro Pro Gln Ile Phe Ile Lys Asn Thr Pro Val Pro Ser Asn
                645                 650                 655
Pro Ala Thr Thr Tyr Thr Thr Ala Lys Tyr Asn Ser Phe Ile Thr Gln
            660                 665                 670
Tyr Ser Thr Gly Gln Val Thr Val Glu Ile Asp Trp Glu Leu Gln Lys
                675                 680                 685
Glu Thr Ser Lys Lys Trp Asn Pro Glu Ile Gln Phe Thr Ser Asn Tyr
            690                 695                 700
Asn Gly Thr Asp Thr Leu Gly Phe Ala Pro Asp Ala Ala Gly Asp Tyr
705                 710                 715                 720
Thr Glu Pro Arg Ala Ile Gly Thr Arg Tyr Leu Thr Arg Pro Leu
                725                 730                 735

<210> SEQ ID NO 6
<211> LENGTH: 589
<212> TYPE: PRT
<213> ORGANISM: Artificial Sequence
<220> FEATURE:
<223> OTHER INFORMATION: consensus VP2 (protein)

<400> SEQUENCE: 6

Met Ala Pro Pro Lys Lys Lys Thr Lys Gln Glu Tyr Lys Asp Thr
1               5                   10                  15
Leu Glu Ala Ile Pro Pro Ser Arg Glu Glu Gln Thr Pro Gln Lys
                20                  25                  30
Gly Ser Ser Ala Ser Lys Asn Gly Ala Ser Ser Ala Ala Ala Ala
            35                  40                  45
Ala Pro Ser Asn Leu Gly Ser Gly Ile Met Ala Glu Gly Gly Ala
        50                  55                  60
Pro Met Gly Asp Asn Gln Gln Gly Ala Asp Gly Val Gly Asn Ala Ser
65                  70                  75                  80
Gly Asn Trp His Cys Asp Ser His Trp Met Gly Asp Lys Val Val Thr
                85                  90                  95
Arg Thr Thr Arg Thr Trp Val Leu Pro Thr Tyr Asn Asn His Leu Tyr
            100                 105                 110
Gln Ala Ile Asp Glu Asn Thr Thr Leu Gly Ser Ala Asn Phe Tyr
                115                 120                 125
Gly Phe Ser Thr Pro Trp Gly Tyr Phe Asp Phe Asn Arg Phe His Cys
            130                 135                 140
His Phe Ser Pro Arg Asp Trp Gln Arg Leu Ile Asn Asn Asn Trp Gly
```

```
                145                 150                 155                 160
            Ile Arg Pro Arg Ser Leu Arg Phe Lys Leu Phe Asn Ile Gln Val Lys
                            165                 170                 175

Glu Val Thr Thr Thr Ser Gly Glu Thr Thr Ile Ala Asn Asn Leu Thr
                            180                 185                 190

Ser Thr Val Gln Val Phe Ala Asp Glu Glu Met His Leu Pro Tyr Val
                            195                 200                 205

Leu Gly Ser Ala His Asp Gly Cys Phe Pro Phe Pro Pro Asp Ile
            210                 215                 220

Tyr Met Leu Pro Gln Tyr Gly Tyr Cys Thr Leu Asp Tyr Gln Gly Leu
            225                 230                 235                 240

Thr Thr Asp Arg Ser Ala Phe Tyr Cys Leu Glu Tyr Phe Pro Ser Gln
                            245                 250                 255

Met Leu Arg Thr Gly Asn Asn Phe Glu Leu Thr Tyr Asn Phe Glu Lys
                            260                 265                 270

Leu Pro Phe His Ser Met Trp Met His Asn Gln Ser Leu Asp Arg Ile
                            275                 280                 285

Met Asn Pro Leu Ile Asp Gln Tyr Leu Tyr Arg Phe Ala Ser Lys Thr
                            290                 295                 300

Gly Asn Thr Trp Thr Tyr Gln Lys Gly Ser Lys Asp Lys Thr Ala
            305                 310                 315                 320

Gln Ala Arg Asn Trp Leu Pro Gly Pro Ser Ile Arg Asn Gln Pro Leu
                            325                 330                 335

Tyr Ser Ser Gly Asn Gln Thr Asn Leu Ser Gly Tyr Asp Ile Ala Pro
                            340                 345                 350

Lys Thr Glu Val Asn Glu Lys Gln Met Thr Val Phe Pro Gly Leu Ser
                            355                 360                 365

Met Ala Thr Glu Asn Glu Arg Ser Gly Thr Ile Lys Glu Gln Pro Thr
            370                 375                 380

Ser Asn Leu Leu Ile Phe Ala Asn Lys Ala Asp Ala Ala Thr Ser Gln
            385                 390                 395                 400

Thr Thr Ser Ser Val Gly Ser Thr Ala Thr Leu Leu Val Thr Asn Glu
                            405                 410                 415

Asn Glu Val Lys Thr Val Asn Pro Ser Ala Thr Glu Ala Trp Gly Ser
                            420                 425                 430

Ala Ala Ala Asn Lys Gln Thr Ser Ala Thr Ala Ser Gln Ser Val Ala
                            435                 440                 445

Ile His Ala Gln Gly Val Val Pro Gly Met Val Trp Gln Asp Arg Asp
            450                 455                 460

Ile Tyr Phe Gln Gly Pro Ile Trp Ala Lys Ile Pro His Thr Asp Gly
            465                 470                 475                 480

His Phe His Pro Ser Pro Leu Met Gly Gly Phe Gly Leu Lys His Pro
                            485                 490                 495

Pro Pro Gln Ile Phe Ile Lys Asn Thr Pro Val Pro Ser Asn Pro Ala
                            500                 505                 510

Thr Thr Tyr Thr Thr Ala Lys Tyr Asn Ser Phe Ile Thr Gln Tyr Ser
                            515                 520                 525

Thr Gly Gln Val Thr Val Glu Ile Asp Trp Glu Leu Gln Lys Glu Thr
                            530                 535                 540

Ser Lys Lys Trp Asn Pro Glu Ile Gln Phe Thr Ser Asn Tyr Asn Gly
            545                 550                 555                 560

Thr Asp Thr Leu Gly Phe Ala Pro Asp Ala Ala Gly Asp Tyr Thr Glu
                            565                 570                 575
```

```
Pro Arg Ala Ile Gly Thr Arg Tyr Leu Thr Arg Pro Leu
            580                 585

<210> SEQ ID NO 7
<211> LENGTH: 532
<212> TYPE: PRT
<213> ORGANISM: Artificial Sequence
<220> FEATURE:
<223> OTHER INFORMATION: consensus VP3 (protein)

<400> SEQUENCE: 7

Met Ala Glu Gly Gly Ala Pro Met Gly Asp Asn Gln Gln Gly Ala
1               5                   10                  15

Asp Gly Val Gly Asn Ala Ser Gly Asn Trp His Cys Asp Ser His Trp
            20                  25                  30

Met Gly Asp Lys Val Val Thr Arg Thr Arg Thr Trp Val Leu Pro
            35                  40                  45

Thr Tyr Asn Asn His Leu Tyr Gln Ala Ile Asp Glu Asn Thr Thr Leu
        50                  55                      60

Gly Ser Ala Asn Asn Phe Tyr Gly Phe Ser Thr Pro Trp Gly Tyr Phe
65                  70                  75                  80

Asp Phe Asn Arg Phe His Cys His Phe Ser Pro Arg Asp Trp Gln Arg
                85                  90                  95

Leu Ile Asn Asn Trp Gly Ile Arg Pro Arg Ser Leu Arg Phe Lys
            100                 105                 110

Leu Phe Asn Ile Gln Val Lys Glu Val Thr Thr Thr Ser Gly Glu Thr
            115                 120                 125

Thr Ile Ala Asn Asn Leu Thr Ser Thr Val Gln Val Phe Ala Asp Glu
        130                 135                 140

Glu Met His Leu Pro Tyr Val Leu Gly Ser Ala His Asp Gly Cys Phe
145                 150                 155                 160

Pro Pro Phe Pro Pro Asp Ile Tyr Met Leu Pro Gln Tyr Gly Tyr Cys
                165                 170                 175

Thr Leu Asp Tyr Gln Gly Leu Thr Thr Asp Arg Ser Ala Phe Tyr Cys
            180                 185                 190

Leu Glu Tyr Phe Pro Ser Gln Met Leu Arg Thr Gly Asn Asn Phe Glu
            195                 200                 205

Leu Thr Tyr Asn Phe Glu Lys Leu Pro Phe His Ser Met Trp Met His
        210                 215                 220

Asn Gln Ser Leu Asp Arg Ile Met Asn Pro Leu Ile Asp Gln Tyr Leu
225                 230                 235                 240

Tyr Arg Phe Ala Ser Lys Thr Gly Asn Thr Trp Thr Tyr Gln Lys Gly
                245                 250                 255

Ser Lys Asp Asp Lys Thr Ala Gln Ala Arg Asn Trp Leu Pro Gly Pro
            260                 265                 270

Ser Ile Arg Asn Gln Pro Leu Tyr Ser Ser Gly Asn Gln Thr Asn Leu
            275                 280                 285

Ser Gly Tyr Asp Ile Ala Pro Lys Thr Glu Val Asn Glu Lys Gln Met
        290                 295                 300

Thr Val Phe Pro Gly Leu Ser Met Ala Thr Glu Asn Glu Arg Ser Gly
305                 310                 315                 320

Thr Ile Lys Glu Gln Pro Thr Ser Asn Leu Leu Ile Phe Ala Asn Lys
                325                 330                 335

Ala Asp Ala Ala Thr Ser Gln Thr Ser Ser Val Gly Ser Thr Ala
            340                 345                 350
```

```
Thr Leu Leu Val Thr Asn Glu Asn Glu Val Lys Thr Val Asn Pro Ser
            355                 360                 365
Ala Thr Glu Ala Trp Gly Ser Ala Ala Ala Asn Lys Gln Thr Ser Ala
    370                 375                 380
Thr Ala Ser Gln Ser Val Ala Ile His Ala Gln Gly Val Val Pro Gly
385                 390                 395                 400
Met Val Trp Gln Asp Arg Asp Ile Tyr Phe Gln Gly Pro Ile Trp Ala
                405                 410                 415
Lys Ile Pro His Thr Asp Gly His Phe His Pro Ser Pro Leu Met Gly
            420                 425                 430
Gly Phe Gly Leu Lys His Pro Pro Pro Gln Ile Phe Ile Lys Asn Thr
        435                 440                 445
Pro Val Pro Ser Asn Pro Ala Thr Thr Tyr Thr Thr Ala Lys Tyr Asn
    450                 455                 460
Ser Phe Ile Thr Gln Tyr Ser Thr Gly Gln Val Thr Val Glu Ile Asp
465                 470                 475                 480
Trp Glu Leu Gln Lys Glu Thr Ser Lys Lys Trp Asn Pro Glu Ile Gln
                485                 490                 495
Phe Thr Ser Asn Tyr Asn Gly Thr Asp Thr Leu Gly Phe Ala Pro Asp
            500                 505                 510
Ala Ala Gly Asp Tyr Thr Glu Pro Arg Ala Ile Gly Thr Arg Tyr Leu
        515                 520                 525
Thr Arg Pro Leu
    530

<210> SEQ ID NO 8
<211> LENGTH: 1770
<212> TYPE: DNA
<213> ORGANISM: Artificial Sequence
<220> FEATURE:
<223> OTHER INFORMATION: consensus VP2 (DNA)

<400> SEQUENCE: 8
ctggctccac ctccaaaaaa gaagacaaaa caggaataca agacactct agaggctatt      60 cctcctccta gcagagagga acagactcct cagaagggat cttcagcatc caaaaacgga     120
gcctcatctt cagcagcagc agcagccccc agtaatttgg gatctggtat catggcagaa     180
ggcggtggcg caccaatggg cgacaatcaa cagggtgccg atggagtggg taatgcctcg     240
ggaaattggc attgcgattc ccactggatg ggcgacaaag tcgtcacccg caccaccaga     300
acctgggtcc tgcccaccta caacaaccac ctctaccaag ccatcgacga aatactact      360 ctcggatccg ccaacaactt ctacggattc agcaccccat gggggtactt tgactttaac     420
cgcttccact gccactttctc cccacgtgac tggcaaagac tcatcaacaa caactggggc     480
atccgaccca agcctcag attcaagctg ttcaacatcc aagtcaagga ggtcacgacg     540
acgtcgggcg aaacgaccat cgccaataac cttaccagca cggttcaggt ttttgcggat     600
gaagaaatgc acctcccgta cgtcttaggg agtgcccacg acggtgcttt cctccatttt    660
ccaccagaca tttacatgct gccccaatac gggtactgca ctctggacta tcagggactc     720
accacagaca ggagcgcctt ctactgtctg gagtacttcc cttctcagat gctgagaacg     780
ggcaacaact ttgagcttac ttacaacttt gagaagctgc ctttccacag catgtggatg     840
cacaaccagt ccctgacag gatcatgaat cctctcatcg atcagtacct gtatcgcttc     900
gcctccaaga ctggcaacac atggacatac caaaaaggca gcaagacga caagaccgct    960
```

| | |
|---|---|
| caagccagaa actggcttcc tggaccctcc atcagaaatc agcctctgta ctcgagtggt | 1020 |
| aatcaaacca acctctcggg atacgatatc gctccaaaaa cagaagtcaa cgagaaacag | 1080 |
| atgactgtgt ttcctggact ttctatggcc accgaaaacg agaggagcgg aaccatcaaa | 1140 |
| gagcagccaa cgtccaatct gctcatcttt gccaacaaag cggatgcggc tacctctcag | 1200 |
| accacttcta gcgtgggcag tacagcgaca ctcctggtca ccaacgaaaa cgaagtcaag | 1260 |
| actgtcaatc cctccgccac cgaagcgtgg ggttcggctg cggccaacaa acagacatct | 1320 |
| gctaccgcct ctcaaagcgt ggctattcac gctcaaggcg tggtgccagg catggtctgg | 1380 |
| caagacagag acatctactt tcagggcccc atctgggcca agatcccgca tacagatgga | 1440 |
| cactttcacc catctcctct catgggtgga ttcggactca acatcctcc tccacaaatt | 1500 |
| ttcattaaaa acactcctgt cccctccaat cctgctacca cgtacaccac cgccaagtac | 1560 |
| aactccttca tcacccagta ctccaccggt caagtgactg tggagattga ctgggaactc | 1620 |
| cagaaggaga cctccaaaaa gtggaacccc gagatccagt tcacctccaa ttacaacggg | 1680 |
| acagacacgc tcggattcgc tccagatgcc gctggagact acaccgaacc acgtgccatt | 1740 |
| ggcacccgtt acctcacccg tcccctgtaa | 1770 |

<210> SEQ ID NO 9
<211> LENGTH: 1599
<212> TYPE: DNA
<213> ORGANISM: Artificial Sequence
<220> FEATURE:
<223> OTHER INFORMATION: consensus VP3 (DNA)

<400> SEQUENCE: 9

| | |
|---|---|
| atggcagaag gcggtggcgc accaatgggc gacaatcaac agggtgccga tggagtgggt | 60 |
| aatgcctcgg gaaattggca ttgcgattcc cactggatgg cgacaaagt cgtcacccgc | 120 |
| accaccagaa cctgggtcct gcccacctac aacaaccacc tctaccaagc catcgacgag | 180 |
| aatactactc tcgatccgc caacaacttc tacggattca gcaccccatg ggggtacttt | 240 |
| gactttaacc gcttccactg ccacttctcc ccacgtgact ggcaaagact catcaacaac | 300 |
| aactggggca tccgacccag aagcctcaga ttcaagctgt tcaacatcca agtcaaggag | 360 |
| gtcacgacga cgtcgggcga aacgaccatc gccaataacc ttaccagcac ggttcaggtt | 420 |
| tttgcggatg aagaaatgca cctcccgtac gtcttaggga gtgcccacga cgggtgcttt | 480 |
| cctccatttc caccagacat ttacatgctg ccccaatacg ggtactgcac tctggactat | 540 |
| cagggactca ccacagacag gagcgccttc tactgtctgg agtacttccc ttctcagatg | 600 |
| ctgagaacgg gcaacaactt tgagcttact tacaactttg agaagctgcc tttccacagc | 660 |
| atgtggatgc acaaccagtc cctggacagg atcatgaatc ctctcatcga tcagtacctg | 720 |
| tatcgcttcg cctccaagac tggcaacaca tggacatacc aaaaaggcag caaagacgac | 780 |
| aagaccgctc aagccagaaa ctggcttcct ggaccctcca tcagaaatca gcctctgtac | 840 |
| tcgagtggta atcaaaccaa cctctcggga tacgatatcg ctccaaaaac agaagtcaac | 900 |
| gagaaacaga tgactgtgtt tcctggactt tctatggcca ccgaaaacga gaggagcgga | 960 |
| accatcaaag agcagccaac gtccaatctg ctcatctttg ccaacaaagc ggatgcggct | 1020 |
| acctctcaga ccacttctag cgtgggcagt acagcgacac tcctggtcac caacgaaaac | 1080 |
| gaagtcaaga ctgtcaatcc ctccgccacc gaagcgtggg gttcggctgc ggccaacaaa | 1140 |
| cagacatctg ctaccgcctc tcaaagcgtg gctattcacg ctcaaggcgt ggtgccaggc | 1200 |
| atggtctggc aagacagaga catctacttt cagggcccca tctgggccaa gatcccgcat | 1260 |

```
acagatggac actttcaccc atctcctctc atgggtggat tcggactcaa acatcctcct      1320
ccacaaattt tcattaaaaa cactcctgtc ccctccaatc ctgctaccac gtacaccacc      1380
gccaagtaca actccttcat cacccagtac tccaccggtc aagtgactgt ggagattgac      1440
tgggaactcc agaaggagac ctccaaaaag tggaaccccg agatccagtt cacctccaat      1500
tacaacggga cagacacgct cggattcgct ccagatgccg ctggagacta caccgaacca      1560
cgtgccattg caccccgtta cctcacccgt ccctgtaa                              1599

<210> SEQ ID NO 10
<211> LENGTH: 66
<212> TYPE: DNA
<213> ORGANISM: Artificial Sequence
<220> FEATURE:
<223> OTHER INFORMATION: AAV_univ_lin primer
<220> FEATURE:
<221> NAME/KEY: misc_feature
<222> LOCATION: (28)..(28)
<223> OTHER INFORMATION: n is a, c, g, or t
<220> FEATURE:
<221> NAME/KEY: misc_feature
<222> LOCATION: (30)..(30)
<223> OTHER INFORMATION: n is a, c, g, or t
<220> FEATURE:
<221> NAME/KEY: misc_feature
<222> LOCATION: (37)..(37)
<223> OTHER INFORMATION: n is a, c, g, or t
<220> FEATURE:
<221> NAME/KEY: misc_feature
<222> LOCATION: (43)..(43)
<223> OTHER INFORMATION: n is a, c, g, or t

<400> SEQUENCE: 10
aatgatacgg cgaccaccga gatctccntn ytayggntgy gtnaaytgga cyaaysaraa      60 yttycc                                                                66

<210> SEQ ID NO 11
<211> LENGTH: 55
<212> TYPE: DNA
<213> ORGANISM: Artificial Sequence
<220> FEATURE:
<223> OTHER INFORMATION: AAV2_3085_rev+N primer
<220> FEATURE:
<221> NAME/KEY: misc_feature
<222> LOCATION: (31)..(31)
<223> OTHER INFORMATION: n is a, c, g, or t
<220> FEATURE:
<221> NAME/KEY: misc_feature
<222> LOCATION: (44)..(44)
<223> OTHER INFORMATION: n is a, c, g, or t

<400> SEQUENCE: 11
caagcagaag acggcatacg agcccccart ngttrttrat ragnckytgc cagtc           55

<210> SEQ ID NO 12
<211> LENGTH: 49
<212> TYPE: DNA
<213> ORGANISM: Artificial Sequence
<220> FEATURE:
<223> OTHER INFORMATION: AAV2_3095_rev+N primer
<220> FEATURE:
<221> NAME/KEY: misc_feature
<222> LOCATION: (24)..(24)
<223> OTHER INFORMATION: n is a, c, g, or t
<220> FEATURE:
<221> NAME/KEY: misc_feature
<222> LOCATION: (26)..(27)
<223> OTHER INFORMATION: n is a, c, g, or t
<220> FEATURE:
```

```
<221> NAME/KEY: misc_feature
<222> LOCATION: (35)..(35)
<223> OTHER INFORMATION: n is a, c, g, or t
<220> FEATURE:
<221> NAME/KEY: misc_feature
<222> LOCATION: (48)..(48)
<223> OTHER INFORMATION: n is a, c, g, or t

<400> SEQUENCE: 12
caagcagaag acggcatacg agcnannccc cartngttrt tratragnc          49
```

AAV CAPSID POLYNUCLEOTIDES AND POLYPEPTIDES AND VIRIONS CONTAINING THE SAME

FIELD OF INVENTION

The present disclosure relates generally to adeno-associated virus (AAV) nucleic acid molecules derived from marsupial specimens, and their encoded polypeptides. The disclosure also relates to vectors, including AAV vectors, comprising and/or produced using the nucleic acid molecules. The disclosure also relates to uses of the nucleic acid molecules, polypeptides and vectors.

CROSS REFERENCE TO RELATED APPLICATIONS

This application is a National Stage application under 35 U.S.C. § 371 of International Application No. PCT/AU2019/050556, filed on May 31, 2019, which claims priority to Australian Provisional Application No. 2018901931 entitled "AAV polynucleotides, polypeptides and virions" filed 31 May 2018, the contents of which are incorporated herein by reference in their entirety.

SEQUENCE LISTING

The present application is being filed along with a Sequence Listing in electronic format. The Sequence Listing is provided as a file entitled 229752008400SeqList.txt, created Nov. 23, 2020, which is 39,539 bytes in size. The information in the electronic format of the Sequence Listing is incorporated by reference in its entirety.

BACKGROUND OF THE DISCLOSURE

Gene therapy has most commonly been investigated and achieved using viral vectors, with notable recent advances being based on adeno-associated viral vectors. Adeno-associated virus (AAV) is a replication-deficient parvovirus, the single-stranded DNA genome of which is about 4.7 kb in length. The AAV genome includes inverted terminal repeat (ITRs) at both ends of the molecule, flanking two open reading frames: rep and cap. The cap gene encodes three capsid proteins: VP1, VP2 and VP3. The three capsid proteins typically assemble in a ratio of 1:1:10 to form the AAV capsid, although AAV capsids containing only VP3, or VP1 and VP3, or VP2 and VP3, have been produced. The cap gene also encodes the assembly activating protein (AAP) from an alternative open reading frame. AAP promotes capsid assembly, acting to target the capsid proteins to the nucleolus and promote capsid formation. The rep gene encodes four regulatory proteins: Rep78, Rep68, Rep52 and Rep40. These Rep proteins are involved in AAV genome replication.

The ITRs are involved in several functions, in particular integration of the AAV DNA into the host cell genome, as well as genome replication and packaging. When AAV infects a host cell, the viral genome can integrate into the host's chromosomal DNA resulting in latent infection of the cell. Thus, AAV can be exploited to introduce heterologous sequences into cells. In a natural system, a helper virus (for example, adenovirus or herpesvirus) provides genes that allow for production of AAV virus in the infected cell. In the case of adenovirus, genes E1A, E1B, E2A, E4 and VA provide helper functions. Upon infection with a helper virus, the AAV provirus is rescued and amplified, and both AAV and adenovirus are produced.

Replication deficient recombinant AAV (sometimes also referred to as AAV vectors) containing a genome that lacks some, most or all of the native AAV genome and instead contains one or more heterologous sequences flanked by the ITRs have been successfully used in gene therapy settings. One of the major problems associated with the use of recombinant AAV is the pre-existing immunity in patients to AAV, particularly the AAV serotypes that most commonly circulate among humans, such as AAV2. The immune response is almost entirely directed to the capsid protein. Another problem is the limited tropism of the commonly used recombinant AAV vectors. Thus, there is a continued need for alternative recombinant AAV virions, in particular those that contain capsid proteins that are distinct from those of the AAV serotypes in circulation and that are resistant to pre-existing immunity to AAV, and those with broader or different tropism.

SUMMARY OF THE DISCLOSURE

The present disclosure is predicated in part on the identification of adeno-associated virus (AAV) sequences from marsupial species. A consensus sequence for the capsid gene (cap) of the marsupial AAV (mAAV) was deduced and used to generate AAV vectors (i.e. rAAV virions) with novel capsids and also chimeric capsid genes. The mAAV cap and the encoded capsid polypeptides (i.e. VP1, VP2 and VP3) have limited homology to other known AAV. As a result, AAV vectors comprising these capsid polypeptides or fragments thereof (e.g. chimeric capsid polypeptides comprising mAAV sequence) may be particularly useful for gene therapy in humans because pre-existing anti-AAV antibodies are unlikely to cross-react with the virions.

In one aspect, the present disclosure provides an isolated capsid polypeptide, comprising the sequence of amino acids set forth in SEQ ID NO:7 or a sequence having at least or about 95% sequence identity to the sequence set forth in SEQ ID NO:7 (e.g. it comprises a mAAV VP3 capsid polypeptide).

In some embodiments, the isolated capsid polypeptide of claim 1 comprises the sequence of amino acids set forth in SEQ ID NO:6 or a sequence having at least or about 95% sequence identity to the sequence set forth in SEQ ID NO:6 (e.g. it comprises a mAAV VP2 capsid polypeptide). In still further embodiments, the polypeptide comprises the sequence of amino acids set forth in SEQ ID NO:5 or a sequence having at least or about 95% sequence identity to the sequence set forth in SEQ ID NO:5 (e.g. it comprises a mAAV VP1 capsid polypeptide). In particular examples, the isolated capsid polypeptide of the present disclosure comprises a region selected from among a phospholipase A2 (PLA2) domain set forth in amino acid residues 53-112 of SEQ ID NO:5; a variable region (VR)-I set forth in amino acid residues 263-271 of SEQ ID NO:5; a VR-II set forth in amino acid residues 227-231 of SEQ ID NO:5; a VR-III set forth in amino acid residues 381-389 of SEQ ID NO:5, a VR-IV set forth in amino acid residues 449-462 of SEQ ID NO:5; a VR-V set forth in amino acid residues 481-496 of SEQ ID NO:5; a VR-VI set forth in amino acid residues 517-535 of SEQ ID NO:5; a VR-VII set forth in amino acid residues 538-556 of SEQ ID NO:5; a VR-VIII set forth in amino acid residues 579-595 of SEQ ID NO:5; or VR-IX set forth in amino acid residues 704-711 of SEQ ID NO:5; or corresponding residues in a sequence having at least 95% sequence identity to the sequence set forth in SEQ ID NO:5.

In another aspect, the disclosure provides a chimeric capsid polypeptide, comprising: (a) at least or about 35, 40, 45, 50, 55, 60, 65, 75, 80, 85, 90, 95, 100, 120, 140, 160, 180, 200, 250, 300, 350, 400, 450, 500, 550, 600, 650, or 700 contiguous amino acids of an mAAV capsid polypeptide set forth in SEQ ID NO:5 or an mAAV capsid polypeptide having at least or about 95% sequence identity to the mAAV capsid polypeptide set forth in SEQ ID NO: 5; and (b) contiguous amino acids from one or more capsid polypeptides other than the mAAV capsid polypeptide set forth in SEQ ID NO:5 or an mAAV capsid polypeptide having at least or about 95% sequence identity to the mAAV capsid polypeptide set forth in SEQ ID NO: 5.

In some examples, the chimeric capsid polypeptide comprises at least or about 35, 40, 45, 50, 55, 60, 65, 75, 80, 85, 90, 95, 100, 120, 140, 160, 180, 200, 250, 300, 350, 400, 450, 500, 550, 600, 650, or 700 contiguous amino acids from one or more capsid polypeptides other than the mAAV capsid polypeptide.

The chimeric capsid polypeptide may comprise one or more regions of the mAAV capsid polypeptide. In one example, the chimeric capsid polypeptide comprises the sequence of amino acids set forth in SEQ ID NO:7 (e.g. a VP3 polypeptide). In other examples, the chimeric capsid polypeptide comprises a region selected from among a phospholipase A2 (PLA2) domain set forth in amino acid residues 53-112 of SEQ ID NO:5; a variable region (VR)-I set forth in amino acid residues 263-271 of SEQ ID NO:5; a VR-II set forth in amino acid residues 227-231 of SEQ ID NO:5; a VR-III set forth in amino acid residues 381-389 of SEQ ID NO:5, a VR-IV set forth in amino acid residues 449-462 of SEQ ID NO:5; a VR-V set forth in amino acid residues 481-496 of SEQ ID NO:5; a VR-VI set forth in amino acid residues 517-535 of SEQ ID NO:5; a VR-VII set forth in amino acid residues 538-556 of SEQ ID NO:5; a VR-VIII set forth in amino acid residues 579-595 of SEQ ID NO:5; and VR-IX set forth in amino acid residues 704-711 of SEQ ID NO:5; or corresponding residues in a sequence having at least 95% sequence identity to the sequence set forth in SEQ ID NO:5.

Also provided are AAV vectors comprising a capsid polypeptide or a chimeric capsid polypeptide described above and herein. In some examples, the AAV vector further comprises a heterologous sequence. The present disclosure also provides a method for introducing a heterologous sequence into a host cell, comprising contacting a host cell with the AAV vector containing a heterologous sequence. Host cells comprising any of the AAV vectors described above and herein are also provided.

In another aspect, the disclosure provides a nucleic acid molecule encoding a capsid polypeptide or chimeric capsid polypeptide described above and herein. In some embodiments, the nucleic acid molecule comprises a sequence set forth in any one of SEQ ID NOs:4, 8 or 9 or a sequence having at least or about 95% sequence identity to the sequence set forth in SEQ ID NOs:4, 8 or 9.

Also provided is a vector (e.g. a plasmid, cosmid, phage or transposon) comprising a nucleic acid molecule described above and herein, and a host cell comprising such nucleic acid molecules or vectors.

In a further aspect, the disclosure provides a method for producing a chimeric capsid gene, comprising (a) providing two or more AAV capsid genes from two or more AAV, wherein at least one capsid gene encodes a capsid polypeptide described above and herein; (b) digesting the AAV capsid genes into fragments; and (c) reassembling the fragments using PCR to form a chimeric capsid gene. In some examples, the resulting chimeric capsid gene encodes a region or domain of a capsid polypeptide described above and herein.

Typically, in such methods, a library of chimeric capsid genes is produced. In some embodiments, the method then further comprises inserting the chimeric capsid gene into a vector, such as a plasmid. In some instances, this can produce a library of vectors (e.g. plasmids). In still further examples, the method then comprises introducing the plasmid into a host cell under conditions sufficient to produce an AAV or AAV vector, thereby producing an AAV or AAV vector comprising a chimeric capsid. In some instances, a library of AAV or AAV vectors is produced.

The present disclosure also provides a chimeric capsid gene, a library of chimeric capsid genes, a vector, a library of vectors, an AAV or AAV vector, and a library of AAV or AAV vectors, produced by the methods described above and herein.

A particular aspect of the present disclosure provides a method for producing an AAV vector, comprising: (a) introducing into a cell a nucleic acid molecule encoding a capsid polypeptide or chimeric capsid polypeptide described above and herein, an AAV rep gene, a heterologous sequence flanked by inverted terminal repeats, and helper functions for generating a productive AAV infection; and allowing assembly of an AAV vector comprising a capsid comprising the capsid polypeptide or chimeric capsid polypeptide, wherein the capsid encapsidates the heterologous sequence.

BRIEF DESCRIPTION OF THE DRAWINGS

Embodiments of the disclosure are described herein, by way of non-limiting example only, with reference to the following drawings.

DETAILED DESCRIPTION

Figure 1:
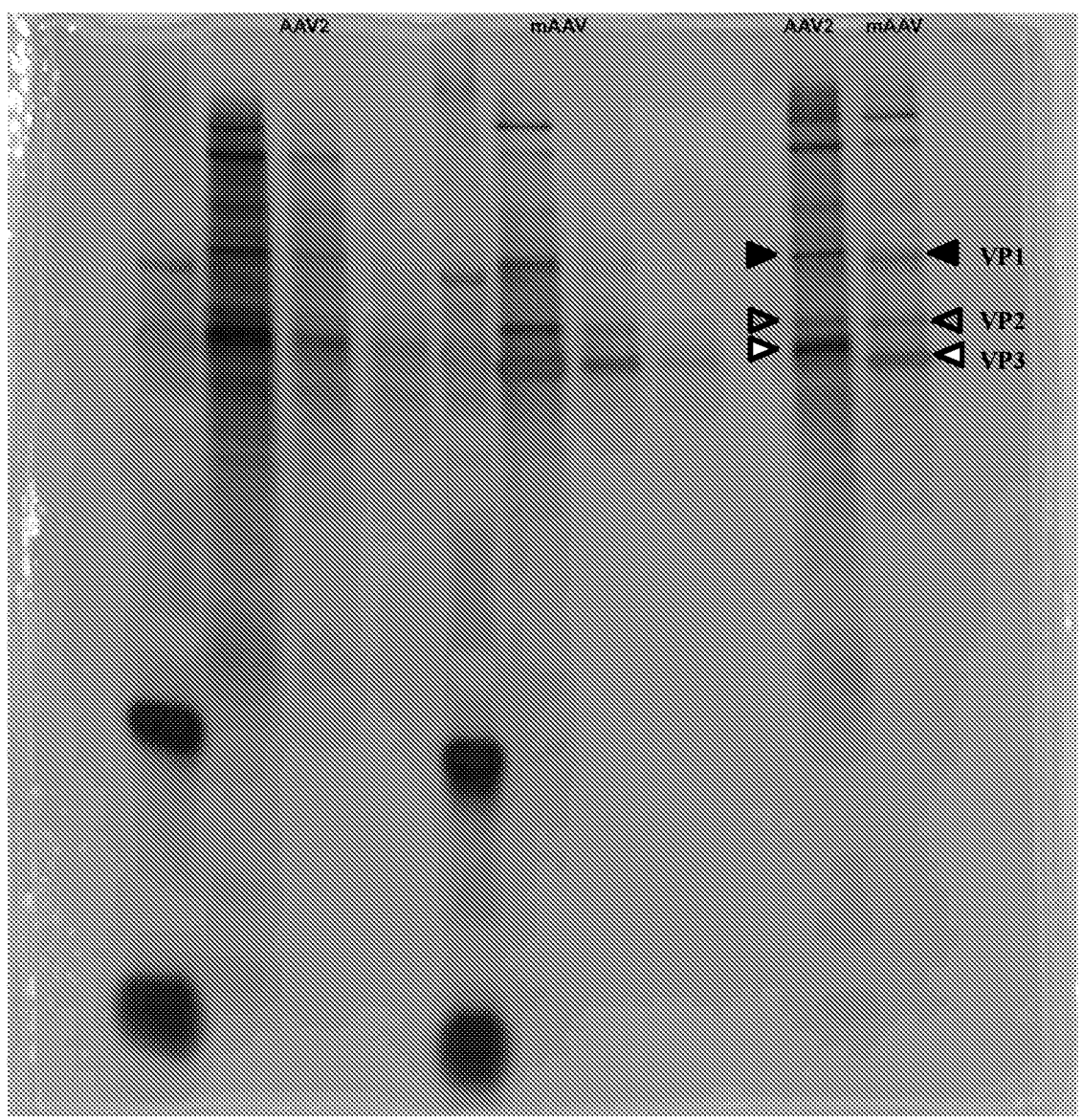
FIG. 1 shows silver staining of mAAV and AAV2 virions following denaturing gel electrophoresis. VP1, VP2 and VP3 are indicated by black, grey and white arrowheads, respectively.

Unless defined otherwise, all technical and scientific terms used herein have the same meaning as is commonly understood by one of skill in the art to which the disclosure belongs. All patents, patent applications, published applications and publications, databases, websites and other published materials referred to throughout the entire disclosure, unless noted otherwise, are incorporated by reference in their entirety. In the event that there is a plurality of definitions for terms, those in this section prevail. Where reference is made to a URL or other such identifier or address, it understood that such identifiers can change and particular information on the internet can come and go, but equivalent information can be found by searching the internet. Reference to the identifier evidences the availability and public dissemination of such information.

As used herein, the singular forms "a", "an" and "the" also include plural aspects (i.e. at least one or more than one) unless the context clearly dictates otherwise. Thus, for example, reference to "a polypeptide" includes a single polypeptide, as well as two or more polypeptides.

In the context of this specification, the term "about," is understood to refer to a range of numbers that a person of skill in the art would consider equivalent to the recited value in the context of achieving the same function or result.

Throughout this specification and the claims which follow, unless the context requires otherwise, the word "comprise", and variations such as "comprises" and "comprising", will be understood to imply the inclusion of a stated integer or step or group of integers or steps but not the exclusion of any other integer or step or group of integers or steps.

As used herein, a "vector" includes reference to both polynucleotide vectors and viral vectors, each of which are capable of delivering a transgene contained within the vector into a host cell. Vectors can be episomal, i.e., do not integrate into the genome of a host cell, or can integrate into the host cell genome. The vectors may also be replication competent or replication-deficient. Exemplary polynucleotide vectors include, but are not limited to, plasmids, cosmids and transposons. Exemplary viral vectors for the purposes of the present invention include AAV vectors.

As used herein, "adeno-associated viral vector" or AAV vector refers to a vector derived from an adeno-associated virus, including without limitation, AAV1, AAV2, AAV3, AAV4, AAV5, AAV6, AAV7, AAV8, AAV9, AAV10, AAV11, AAV12, AAV13, AAV from other clades, and synthetic AAV (i.e. synthetic AAV capsid proteins). In some embodiments of the present disclosure, the AAV vectors comprise a mAAV capsid. An AAV vector may also be referred to herein as "recombinant AAV", "rAAV", "recombinant AAV virion", "rAAV virion," and "rAAV particle". AAV vectors are replication-defective viruses that include an AAV capsid shell encapsidating an AAV genome. The AAV genome (also referred to as the vector genome, recombinant AAV genome or rAAV genome) comprises a transgene flanked on both sides by functional AAV ITRs. Typically, one or more of the wild-type AAV genes have been deleted from the genome in whole or part, preferably the rep and/or cap genes. Functional ITR sequences are necessary for the rescue, replication and packaging of the vector genome into the AAV vector. The AAV vector can be utilized for the purpose of transferring heterologous sequences into cells either in vitro or in vivo.

The term "ITR" refers to an inverted terminal repeat at either end of the AAV genome. This sequence can form hairpin structures and is involved in AAV DNA replication and rescue, or excision, from prokaryotic plasmids. ITRs for use in the present disclosure need not be the wild-type nucleotide sequences, and may be altered, e.g., by the insertion, deletion or substitution of nucleotides, as long as the sequences provide for functional rescue, replication and packaging of rAAV.

As used herein, "functional" with reference to a capsid polypeptide means that the polypeptide can self assemble or assemble with different capsid polypeptides to produce the proteinaceous shell (capsid) of an AAV virion. It is to be understood that not all capsid polypeptides in a given host cell assemble into AAV capsids. Preferably, at least 25%, at least 50%, at least 75%, at least 85%, at least 90%, at least 95% of all AAV capsid polypeptide molecules assemble into AAV capsids. Suitable assays for measuring this biological activity are described e.g. in Smith-Arica and Bartlett (2001), Curr Cardiol Rep 3(1): 43-49.

"AAV helper functions" or "helper functions" refer to functions that allow AAV to be replicated and packaged by a host cell. AAV helper functions can be provided in any of a number of forms, including, but not limited to, as a helper virus or as helper virus genes which aid in AAV replication and packaging. Helper virus genes include, but are not limited to, adenoviral helper genes such as E1A, E1B, E2A, E4 and VA. Helper viruses include, but are not limited to, adenoviruses, herpesviruses, poxviruses such as vaccinia, and baculovirus. The adenoviruses encompass a number of different subgroups, although Adenovirus type 5 of subgroup C (Ad5) is most commonly used. Numerous adenoviruses of human, non-human mammalian and avian origin are known and are available from depositories such as the ATCC. Viruses of the herpes family, which are also available from depositories such as ATCC, include, for example, herpes simplex viruses (HSV), Epstein-Barr viruses (EBV), cytomegaloviruses (CMV) and pseudorabies viruses (PRV). Baculoviruses available from depositories include *Autographa californica* nuclear polyhedrosis virus.

As used herein, "corresponding nucleotides" or "corresponding amino acid residues" refer to nucleotides or amino acids that occur at aligned loci. The sequences of related or variant polynucleotides or polypeptides are aligned by any method known to those of skill in the art. Such methods typically maximize matches (e.g. identical nucleotides or amino acids at positions), and include methods such as using manual alignments and by using the numerous alignment programs available (for example, BLASTN, BLASTP, ClustlW, ClustlW2, EMBOSS, LALIGN, Kalign, etc) and others known to those of skill in the art. By aligning the sequences of polynucleotides, one skilled in the art can identify corresponding nucleotides. For example, by aligning the mAAV capsid polypeptide set forth in SEQ ID NO:5 with another AAV capsid polypeptide, one of skill in the art can identify amino acids residues within the other AAV polypeptide that correspond to various regions or residues, such as the VR-I region.

A "heterologous sequence" as used herein refers to nucleic acid sequence present in a polynucleotide, vector, or host cell that is not naturally found in the polynucleotide, vector, or host cell or is not naturally found at the position that it is at in the polynucleotide, vector, or host cell, i.e. is non-native. A "heterologous sequence" can encode a peptide or polypeptide, or a polynucleotide that itself has a function or activity, such as an antisense or inhibitory oligonucleotide, including antisense DNA and RNA (e.g. miRNA, siRNA, and shRNA). In some examples, the heterologous sequence is a stretch of nucleic acids that is essentially homologous to a stretch of nucleic acids in the genomic DNA of an animal, such that when the heterologous sequence is introduced into a cell of the animal, homologous recombination between the heterologous sequence and the genomic DNA can occur. In one example, the heterologous sequence is a functional copy of a gene for introduction into a cell that has a defective/mutated copy.

As used herein, the term "operably-linked" with reference to a promoter and a coding sequence means that the transcription of the coding sequence is under the control of, or driven by, the promoter.

The term "host cell" refers to a cell, such as a mammalian cell, that has introduced into it exogenous DNA, such as a vector. The term includes the progeny of the original cell into which the exogenous DNA has been introduced. Thus, a "host cell" as used herein generally refers to a cell that has been transfected or transduced with exogenous DNA.

As used herein, "isolated" with reference to a nucleic acid molecule means that the nucleic acid molecule is substantially free of cellular material or other contaminating proteins from the cells from which the nucleic acid molecule is derived, or substantially free from chemical precursors or other chemicals when chemically synthesized.

The term "subject" as used herein refers to an animal, in particular a mammal and more particularly a primate including a lower primate and even more particularly, a human who can benefit from the present invention. A subject regardless of whether a human or non-human animal or embryo may be referred to as an individual, subject, animal, patient, host or recipient. The present disclosure has both human and veterinary applications. For convenience, an "animal" specifically includes livestock animals such as cattle, horses, sheep, pigs, camelids, goats and donkeys, as well as domestic animals, such as dogs and cats. With respect to horses, these include horses used in the racing industry as well as those used recreationally or in the livestock industry. Examples of laboratory test animals include mice, rats, rabbits, guinea pigs and hamsters. Rabbits and rodent animals, such as rats and mice, provide a convenient test system or animal model as do primates and lower primates. In some embodiments, the subject is human.

It will be appreciated that the above described terms and associated definitions are used for the purpose of explanation only and are not intended to be limiting.

TABLE 1

Brief Description of the Sequences

| SEQ ID NO. | Description |
|---|---|
| 1 | Consensus mAAV nucleotide sequence |
| 2 | Consensus mAAV cap gene (lacking 10 aa C terminus; coding sequence) |
| 3 | Consensus mAAV capsid protein (VP1; lacking 10 aa C terminus) |
| 4 | Consensus mAAV cap gene |
| 5 | Consensus mAAV capsid protein (VP1) |
| 6 | Consensus mAAV capsid protein (VP2) |
| 7 | Consensus mAAV capsid protein (VP3) |
| 8 | Consensus mAAV capsid (VP2) coding sequence |
| 9 | Consensus mAAV capsid (VP3) coding sequence |
| 10 | AAV_univ_lin primer |
| 11 | AAV2_3085_rev + N primer |
| 12 | AAV2_3095_rev + N primer | mAAV Capsid Polypeptides and Nucleic Acid Molecules

The present disclosure is predicated in part on the identification of adeno-associated virus (AAV) sequences in marsupial specimens. As described herein, the marsupial AAV (mAAV) sequences comprise the cap gene which encodes one or more capsid polypeptides, including VP1, VP2 and/or VP3 protein. Thus, provided herein are polypeptides comprising all or a portion of the mAAV capsid polypeptides, including polypeptides comprising all or a portion of the VP1 protein, VP2 protein and/or the VP3 protein, and variants thereof. Also provided are nucleic acid molecules encoding all or a portion of the mAAV capsid polypeptides and variants thereof.

Provided herein are isolated capsid polypeptides. The capsid polypeptides of the present disclosure have amino acid sequences that are quite distinct and divergent from other AAV capsid polypeptides described previously, including capsid polypeptides from AAV serotypes that commonly circulate amongst humans. Accordingly, the capsid polypeptides of the present disclosure may be particularly useful for producing AAV vectors for gene therapy.

Capsid polypeptides of the present disclosure include those that contain all or a portion (i.e. a fragment) of a mAAV VP1 protein, such as a VP1 protein having an amino acid sequence set forth in SEQ ID NO:5 or an amino acid sequence having at least or about 70%, 75%, 80%, 85%, 90%, 91%, 92%, 93%, 94%, 95%, 96%, 97%, 98% or 99% sequence identity to a sequence set forth in SEQ ID NO:5. Thus, provided are capsid polypeptides comprising an amino acid sequence set forth in SEQ ID NO:5 or an amino acid sequence having at least or about 70%, 75%, 80%, 85%, 90%, 91%, 92%, 93%, 94%, 95%, 96%, 97%, 98% or 99% sequence identity to a sequence set forth in SEQ ID NO:5.

Also provided are capsid polypeptides that contain all or a portion of the mAAV VP3 protein, such as a VP3 protein with an amino acid sequence set forth in SEQ ID NO:7 (i.e. residues 204-735 of SEQ ID NO:5) or an amino acid sequence having at least or about 70%, 75%, 80%, 85%, 90%, 91%, 92%, 93%, 94%, 95%, 96%, 97%, 98% or 99% sequence identity to a sequence set forth in SEQ ID NO:7. Thus, provided are polypeptides comprising an amino acid sequence set forth in SEQ ID NO:7 or an amino acid sequence having at least or about 70%, 75%, 80%, 85%, 90%, 91%, 92%, 93%, 94%, 95%, 96%, 97%, 98% or 99% sequence identity to a sequence set forth in of SEQ ID NO:7.

Also provided are capsid polypeptides that contain all or a portion of the mAAV VP2 protein, such as a VP2 protein with an amino acid sequence set forth in SEQ ID NO:6 (i.e. residues 147-735 of SEQ ID NO:5, but with a methionine at the start of the polypeptide) or an amino acid sequence having at least or about 70%, 75%, 80%, 85%, 90%, 91%, 92%, 93%, 94%, 95%, 96%, 97%, 98% or 99% sequence identity to a sequence set forth in SEQ ID NO:6. Thus, provided are polypeptides comprising an amino acid sequence set forth in SEQ ID NO:6 or an amino acid sequence having at least or about 70%, 75%, 80%, 85%, 90%, 91%, 92%, 93%, 94%, 95%, 96%, 97%, 98% or 99% sequence identity to a sequence set forth in SEQ ID NO:6.

The capsid polypeptides of the present disclosure include those comprising a fragment of a mAAV VP1, VP2 or VP3 protein, such as a fragment of a polypeptide comprising an amino acid set forth in SEQ ID NO:5, 6 or 7 or a fragment of a polypeptide having an amino acid sequence having at least or about 70%, 75%, 80%, 85%, 90%, 91%, 92%, 93%, 94%, 95%, 96%, 97%, 98% or 99% sequence identity to the sequence set forth in SEQ ID NO:5, 6 or 7. The fragment may be of any length but is typically at least 35 amino acids long. Exemplary fragments include those that comprise at least or about 35, 40, 45, 50, 55, 60, 65, 75, 80, 85, 90, 95, 100, 120, 140, 160, 180, 200, 250, 300, 350, 400, 450, 500, 550, 600, 650, or 700 contiguous amino acids of a polypeptide having an amino acid sequence set forth in SEQ ID NO: 5, 6 or 7 or an amino acid sequence having at least or about 70%, 75%, 80%, 85%, 90%, 91%, 92%, 93%, 94%, 95%, 96%, 97%, 98% or 99% sequence identity to the sequence set forth in SEQ ID NO: 5, 6 or 7. Exemplary fragments include those containing the VP2 protein (e.g. SEQ ID NO:6; corresponding to amino acid residues 147-735 of SEQ ID NO:5), VP3 protein (e.g. SEQ ID NO:7; corresponding to amino acid residues 204-735 of SEQ ID NO:5), those that contain the phospholipase A2 (PLA2) domain (amino acid residues 53-112 of SEQ ID NO:5 or corresponding residues in a sequence having at least or about 70%, 75%, 80%, 85%, 90%, 91%, 92%, 93%, 94%, 95%, 96%, 97%, 98% or 99% sequence identity to the sequence set forth in SEQ ID NO:5) and those containing any one or more of the variable regions (VR), including VR-I (amino acid residues 263-271 of SEQ ID NO:5 or corresponding residues in a sequence having at least or about 70%, 75%, 80%, 85%, 90%, 91%, 92%, 93%, 94%, 95%, 96%, 97%, 98% or 99% sequence identity to the sequence set forth in SEQ ID NO:5); VR-II (amino acid residues 227-231 of SEQ ID NO:5 or corresponding residues in a sequence having at least or about 70%, 75%, 80%, 85%, 90%, 91%, 92%, 93%, 94%, 95%, 96%, 97%, 98% or 99% sequence identity to the sequence set forth in SEQ ID NO:5); VR-III (amino acid residues 381-389 of SEQ ID NO:5 or corresponding residues in a sequence having at least or about 70%, 75%, 80%, 85%, 90%, 91%, 92%, 93%, 94%, 95%, 96%, 97%, 98% or 99% sequence identity to the sequence set forth in SEQ ID NO:5); VR-IV (amino acid residues 449-462 of SEQ ID NO:5 or corresponding residues in a sequence having at least or about 70%, 75%, 80%, 85%, 90%, 91%, 92%, 93%, 94%, 95%, 96%, 97%, 98% or 99% sequence identity to the sequence set forth in SEQ ID NO:5); VR-V (amino acid residues 481-496 of SEQ ID NO:5 or corresponding residues in a sequence having at least or about 70%, 75%, 80%, 85%, 90%, 91%, 92%, 93%, 94%, 95%, 96%, 97%, 98% or 99% sequence identity to the sequence set forth in SEQ ID NO:5); VR-VI (amino acid residues 517-535 of SEQ ID NO:5 or corresponding residues in a sequence having at least or about 70%, 75%, 80%, 85%, 90%, 91%, 92%, 93%, 94%, 95%, 96%, 97%, 98% or 99% sequence identity to the sequence set forth in SEQ ID NO:5); VR-VII (amino acid residues 538-556 of SEQ ID NO:5 or corresponding residues in a sequence having at least or about 70%, 75%, 80%, 85%, 90%, 91%, 92%, 93%, 94%, 95%, 96%, 97%, 98% or 99% sequence identity to the sequence set forth in SEQ ID NO:5); VR-VIII (amino acid residues 579-595 of SEQ ID NO:5 or corresponding residues in a sequence having at least or about 70%, 75%, 80%, 85%, 90%, 91%, 92%, 93%, 94%, 95%, 96%, 97%, 98% or 99% sequence identity to the sequence set forth in SEQ ID NO:5); and VR-IX (amino acid residues 704-711 of SEQ ID NO:5 or corresponding residues in a sequence having at least or about 70%, 75%, 80%, 85%, 90%, 91%, 92%, 93%, 94%, 95%, 96%, 97%, 98% or 99% sequence identity to the sequence set forth in SEQ ID NO:5).

The fragments can be functional fragments, i.e. can self-assemble to form an AAV capsid (alone or when present with other capsid polypeptides) that facilitates binding and internalization of the rAAV virion into a host cell. Exemplary of the functional fragments contemplated herein are those that include a mAAV VP3 protein, such as a VP3 protein comprising an amino acid sequence set forth in SEQ ID NO:7 or an amino acid sequence having at least or about 70%, 75%, 80%, 85%, 90%, 91%, 92%, 93%, 94%, 95%, 96%, 97%, 98% or 99% sequence identity to a sequence set forth in SEQ ID NO:7.

In other examples, the fragments are functional when part of a chimeric capsid polypeptide, i.e. the chimeric capsid polypeptide can self assemble or assemble with other capsid polypeptides to the AAV capsid of a rAAV virion. For example, the fragment can be part of a chimeric capsid protein that also contains fragments of capsid proteins from one or more other AAV serotypes, including, but not limited to, AAV1, AAV2, AAV3, AAV4, AAV5, AAV6, AAV7, AAV8, AAV9, AAV10, AAV11, AAV12 or AAV13, other AAV clades and distantly-related AAV, as well as synthetic and modified AAV capsid proteins. Thus, also provided are capsid polypeptides that are chimeric and that include at least or about 35, 40, 45, 50, 55, 60, 65, 75, 80, 85, 90, 95, 100, 120, 140, 160, 180, 200, 250, 300, 350, 400, 450, 500, 550, 600, 650, or 700 contiguous amino acids of the mAAV capsid polypeptide set forth in SEQ ID NO:5 or a capsid polypeptide having at least or about 70%, 75%, 80%, 85%, 90%, 91%, 92%, 93%, 94%, 95%, 96%, 97%, 98% or 99% sequence identity to the mAAV capsid polypeptide set forth in SEQ ID NO:5. As would be appreciated, the chimeric capsid polypeptides also comprise contiguous amino acids from a capsid protein other than the mAAV capsid polypeptide set forth in SEQ ID NO:5 or a polypeptide having at least or about 70%, 75%, 80%, 85%, 90%, 91%, 92%, 93%, 94%, 95%, 96%, 97%, 98% or 99% sequence identity to SEQ ID NO:5. For example, the chimeric capsid polypeptide can include contiguous amino acids from one or more capsid proteins from one or more of AAV1, AAV2, AAV3, AAV4, AAV5, AAV6, AAV7, AAV8, AAV9, AAV10, AAV11, AAV12 or AAV13. The amino acid sequences of numerous AAV capsids have been described and are well known in the art, and can be used to produce the chimeric capsid polypeptides of the disclosure. It is contemplated that the chimeric capsid polypeptides can comprise any number of contiguous amino acids from a capsid protein other than the mAAV capsid polypeptide, provided the resulting chimeric capsid polypeptide is functional. In some embodiments, the chimeric capsid polypeptide comprises at least or about 35, 40, 45, 50, 55, 60, 65, 75, 80, 85, 90, 95, 100, 120, 140, 160, 180, 200, 250, 300, 350, 400, 450, 500, 550, 600, 650, or 700 contiguous amino acids from a capsid protein other than the mAAV capsid polypeptide.

Also contemplated herein are nucleic acid molecules encoding the capsid polypeptides of the present disclosure. Accordingly, provided are nucleic acid molecules encoding a capsid polypeptide comprising the amino acid sequence set forth in any one of SEQ ID NOs: 5-7 or an amino acid sequence having at least or about 70%, 75%, 80%, 85%, 90%, 91%, 92%, 93%, 94%, 95%, 96%, 97%, 98% or 99% sequence identity to the sequence set forth in SEQ ID NO: 5-7 or a fragment thereof. Exemplary nucleic acid molecules include those that comprise the sequence set forth in SEQ ID NO:4, 8 or 9 or a sequence having at least or about 70%, 75%, 80%, 85%, 90%, 91%, 92%, 93%, 94%, 95%, 96%, 97%, 98% or 99% sequence identity to the sequence set forth in SEQ ID NO:4, 8 or 9 or a fragment thereof. In particular examples, the nucleic acid molecules include a promoter operably linked to the nucleic acid encoding the polypeptides, such that the polypeptides can be expressed in a host cell.

Vectors

The present disclosure also provides vectors comprising a nucleic acid molecule that encodes a capsid polypeptide described herein, and vectors comprising a capsid polypeptide described herein. The vectors include nucleic acid vectors that comprise a nucleic acid molecule that encodes a capsid polypeptide described herein, and AAV vectors that have a capsid comprising a capsid polypeptide described herein.

Nucleic Acid Vectors

Vectors of the present disclosure include nucleic acid vectors that comprise nucleic acid that encodes all or a portion of a capsid polypeptide described herein, e.g. that encode polypeptides comprising an amino acid sequence set forth in SEQ ID NO:5, 6 or 7, or an amino acid sequence having at least or about 70%, 75%, 80%, 85%, 90%, 91%, 92%, 93%, 94%, 95%, 96%, 97%, 98% or 99% sequence identity to a sequence set forth in SEQ ID NO:5, 6 or 7, or fragments thereof, as described above. The vectors can be episomal vectors (i.e., that do not integrate into the genome of a host cell), or can be vectors that integrate into the host cell genome. Exemplary vectors that comprise a nucleic acid molecule encoding a capsid polypeptide include, but are not limited to, plasmids, cosmids, transposons and artificial chromosomes. In particular examples, the vectors are plasmids.

Vectors, such as plasmids, suitable for use in bacterial, insect and mammalian cells are widely described and well-known in the art. Those skilled in the art would appreciate that vectors of the present disclosure may also contain additional sequences and elements useful for the replication of the vector in prokaryotic and/or eukaryotic cells, selection of the vector and the expression of a heterologous sequence in a variety of host cells. For example, the vectors of the present disclosure can include a prokaryotic replicon (that is, a sequence having the ability to direct autonomous replication and maintenance of the vector extrachromosomally in a prokaryotic host cell, such as a bacterial host cell. Such replicons are well known in the art. In some embodiments, the vectors can include a shuttle element that makes the vectors suitable for replication and integration in both prokaryotes and eukaryotes. In addition, vectors may also include a gene whose expression confers a detectable marker such as a drug resistance gene, which allows for selection and maintenance of the host cells. Vectors may also have a reportable marker, such as gene encoding a fluorescent or other detectable protein. The nucleic acid vectors will likely also comprise other elements, including any one or more of those described below. Most typically, the vectors will comprise a promoter operably linked to the nucleic acid encoding the capsid protein.

The nucleic acid vectors of the present disclosure can be constructed using known techniques, including, without limitation, the standard techniques of restriction endonuclease digestion, ligation, transformation, plasmid purification, in vitro or chemical synthesis of DNA, and DNA sequencing. The vectors of the present disclosure may be introduced into a host cell using any method known in the art. Accordingly, the present disclosure is also directed to host cells comprising a vector or nucleic acid described herein.

AAV Vectors

Provided herein are AAV vectors comprising a capsid polypeptide described herein, such as a polypeptide comprising all or a portion of a mAAV capsid protein (e.g. a polypeptide comprising the amino acid sequence set forth in SEQ ID NO:5, 6 or 7 or an amino acid sequence having at least or about 70%, 75%, 80%, 85%, 90%, 91%, 92%, 93%, 94%, 95%, 96%, 97%, 98% or 99% sequence identity to a sequence set forth in SEQ ID NO:5, 5 or 7 or a fragment thereof).

The AAV vectors can be produced using, for example, the plasmids described above that encode a capsid polypeptide, and methods for producing AAV vectors having a desired capsid protein are well known in the art. Typically, the AAV vectors will have packaged within them a heterologous sequence as described below.

Typically the methods involve culturing a host cell which contains a nucleic acid molecule encoding an AAV capsid polypeptide (e.g., a nucleic acid molecule encoding a polypeptide comprising the amino acid sequence set forth in SEQ ID NO:5, 6 or 7 or an amino acid sequence having at least or about 70%, 75%, 80%, 85%, 90%, 91%, 92%, 93%, 94%, 95%, 96%, 97%, 98% or 99% sequence identity to a sequence set forth in SEQ ID NO:5, 6 or 7, or a fragment thereof); a functional rep gene; a plasmid containing AAV ITRs flanking a heterologous sequence; and sufficient helper functions to permit packaging of the AAV vector.

In some embodiments, methods for producing a recombinant AAV include introducing into a packaging cell line a nucleic acid molecule, such as a packaging plasmid, encoding mAAV capsid protein or fragment thereof and a rep gene; a plasmid containing AAV ITRs flanking a heterologous sequence; and helper functions for generating a productive AAV infection, and recovering AAV vectors from the supernatant of the packaging cell line. Various types of cells can be used as the packaging cell line. For example, packaging cell lines that can be used include, but are not limited to, HEK 293 cells, HeLa cells, and Vero cells, for example as disclosed in US20110201088.

The helper functions may be provided by one or more helper plasmids or helper viruses comprising adenoviral helper genes. Non-limiting examples of the adenoviral helper genes include E1A, E1B, E2A, E4 and VA, which can provide helper functions to AAV packaging.

In some embodiments, the nucleic acid encoding a capsid polypeptide of the present disclosure is present in a plasmid. The plasmid can further comprise an AAV rep gene. Any AAV rep gene may be used, including, for example, a rep gene is from AAV1, AAV2, AAV3, AAV4, AAV5, AAV6, AAV7, AAV8, AAV9, AAV10, AAV11, AAV12 or AAV13 and any variants thereof.

Helper viruses of AAV are known in the art and include, for example, viruses from the family Adenoviridae and the family Herpesviridae. Examples of helper viruses of AAV include, but are not limited to, SAdV-13 helper virus and SAdV-13-like helper virus described in US20110201088, helper vectors pHELP (Applied Viromics). A skilled artisan will appreciate that any helper virus or helper plasmid of AAV that can provide adequate helper function to AAV can be used herein.

In some instances, AAV vectors are produced using a cell line that stably expresses some of the necessary components for AAV virion production. For example, a plasmid (or multiple plasmids) comprising the nucleic acid encoding a capsid polypeptide of the present disclosure and a rep gene, and a selectable marker, such as a neomycin resistance gene, can be integrated into the genome of a cell (the packaging cells). The packaging cell line can then be transfected with a plasmid comprising a heterologous coding sequence flanked by AAV ITRs and a helper plasmid, or transfected with a plasmid comprising a heterologous coding sequence flanked by AAV ITRs and co-infected with a helper virus (e.g., adenovirus providing the helper functions). The advantages of this method are that the cells are selectable and are suitable for large-scale production of the recombinant AAV. As another non-limiting example, adenovirus or baculovirus rather than plasmids can be used to introduce the nucleic acid encoding the capsid polypeptide, and optionally the rep gene, into packaging cells. As yet another non-limiting example, the heterologous coding sequence flanked by AAV ITRs is stably integrated into the DNA of producer cells, and the helper functions can be provided by a wild-type adenovirus to produce the recombinant AAV.

As noted above, typically, the AAV vectors of the present disclosure also comprise a heterologous sequence. The heterologous sequence may be operably linked to a promoter to facilitate expression of the sequence. The heterologous sequence can encode a peptide or polypeptide, such as a therapeutic peptide or polypeptide, or can encode a polynucleotide or transcript that itself has a function or activity, such as an antisense or inhibitory oligonucleotide, including antisense DNA and RNA (e.g. miRNA, siRNA, and shRNA). In some examples, the heterologous sequence is a stretch of nucleic acids that is essentially homologous to a stretch of nucleic acids in the genomic DNA of an animal, such that when the heterologous sequence is introduced into a cell of the animal, homologous recombination between the heterologous sequence and the genomic DNA can occur. As would be appreciated, the nature of the heterologous sequence is not essential to the present disclosure. In particular embodiments, the vectors comprising the heterologous sequence(s) will be used in gene therapy.

In particular examples, the heterologous sequence encodes a peptide or polypeptide, or polynucleotide, whose expression is of therapeutic use, such as, for example, for the treatment of a disease or disorder. For example, expression of a therapeutic peptide or polypeptide may serve to restore or replace the function of the endogenous form of the peptide or polypeptide that is defective (i.e. gene replacement therapy). In other examples, expression of a therapeutic peptide or polypeptide, or polynucleotide, from the heterologous sequence serves to alter the levels and/or activity of one or more other peptides, polypeptides or polynucleotides in the host cell. Thus, according to particular embodiments, the expression of a heterologous sequence introduced by a vector described herein into a host cell can be used to provide a therapeutic amount of a peptide, polypeptide or polynucleotide to ameliorate the symptoms of a disease or disorder. In other instance, the heterologous sequence is a stretch of nucleic acids that is essentially homologous to a stretch of nucleic acids in the genomic DNA of an animal, such that when the heterologous sequence is introduced into a cell of the animal, homologous recombination between the heterologous sequence and the genomic DNA can occur. Accordingly, the introduction of a heterologous sequence by an AAV vector described herein into a host cell can be used to correct mutations in genomic DNA, which in turn can ameliorate the symptoms of a disease or disorder.

The heterologous sequence in the AAV vector is flanked by 3' and 5' AAV ITRs. AAV ITRs used in the vectors of the disclosure need not have a wild-type nucleotide sequence, and may be altered, e.g., by the insertion, deletion or substitution of nucleotides. Additionally, AAV ITRs may be derived from any of several AAV serotypes, including without limitation, AAV1, AAV2, AAV3, AAV4, AAV5, AAV6, AAV7, AAV8, AAV9, AAV10, AAV11, AAV12 or AAV13. Such ITRs are well known in the art.

As will be appreciated by a skilled artisan, any method suitable for purifying AAV can be used in the embodiments described herein to purify the AAV vectors, and such methods are well known in the art. For example, the AAV vectors can be isolated and purified from packaging cells and/or the supernatant of the packaging cells. In some embodiments, the AAV is purified by separation method using a CsCl gradient. In other embodiments, AAV is purified as described in US20020136710 using a solid support that includes a matrix to which an artificial receptor or receptor-like molecule that mediates AAV attachment is immobilized.

Additional Elements in the Vectors

The vectors of the present disclosure can comprise promoters. In instances where the vector is a nucleic acid vector comprising nucleic acid encoding the capsid polypeptide, the promoter may facilitate expression of the nucleic acid encoding the capsid polypeptide. In instances where the vector is an AAV vector, the promoter may facilitate expression of a heterologous coding sequence, as described above.

In some examples, the promoters are AAV promoters, such as the p5, p19 or p40 promoter. In other examples, the promoters are derived from other sources. Examples of constitutive promoters include, without limitation, the retroviral Rous sarcoma virus (RSV) LTR promoter (optionally with the RSV enhancer), the cytomegalovirus (CMV) promoter (optionally with the CMV enhancer), the SV40 promoter, the dihydrofolate reductase promoter, the β-actin promoter, the phosphoglycerol kinase (PGK) promoter, and the EF1α promoter. Inducible promoters allow regulation of gene expression and can be regulated by exogenously supplied compounds, environmental factors such as temperature, or the presence of a specific physiological state, e.g., acute phase, a particular differentiation state of the cell, or in replicating cells only. Non-limiting examples of inducible promoters regulated by exogenously supplied promoters include the zinc-inducible sheep metallothionine (MT) promoter, the dexamethasone (Dex)-inducible mouse mammary tumor virus (MMTV) promoter, the T7 polymerase promoter system; the ecdysone insect promoter, the tetracycline-repressible system, the tetracycline-inducible system, the RU486-inducible system and the rapamycin-inducible system. Still other types of inducible promoters which may be useful in this context are those which are regulated by a specific physiological state, e.g., temperature, acute phase, a particular differentiation state of the cell, or in replicating cells only. In some embodiments, tissue specific promoters are used. Non-limiting examples of such promoters include the liver-specific thyroxin binding globulin (TBG) promoter, insulin promoter, glucagon promoter, somatostatin promoter, pancreatic polypeptide (PPY) promoter, synapsin-1 (Syn) promoter, creatine kinase (MCK) promoter, mammalian desmin (DES) promoter, a α-myosin heavy chain (a-MHC) promoter, a cardiac Troponin T (cTnT) promoter, beta-actin promoter, and hepatitis B virus core promoter. The selection of an appropriate promoter is well within the ability of one of ordinary skill in the art.

The vectors can also include transcriptional enhancers, translational signals, and transcriptional and translational termination signals. Examples of transcriptional termination signals include, but are not limited to, polyadenylation signal sequences, such as bovine growth hormone (BGH) poly(A), SV40 late poly(A), rabbit beta-globin (RBG) poly(A), thymidine kinase (TK) poly(A) sequences, and any variants thereof. In some embodiments, the transcriptional termination region is located downstream of the posttranscriptional regulatory element. In some embodiments, the transcriptional termination region is a polyadenylation signal sequence.

The vectors can include various posttranscriptional regulatory elements. In some embodiments, the posttranscriptional regulatory element can be a viral posttranscriptional regulatory element. Non-limiting examples of viral posttranscriptional regulatory element include woodchuck hepatitis virus posttranscriptional regulatory element (WPRE), hepatitis B virus posttranscriptional regulatory element (HBVPRE), RNA transport element, and any variants thereof. The RTE can be a rev response element (RRE), for example, a lentiviral RRE. A non-limiting example is bovine immunodeficiency virus rev response element (RRE). In some embodiments, the RTE is a constitutive transport element (CTE). Examples of CTE include, but are not limited to Mason-Pfizer Monkey Virus CTE and Avian Leukemia Virus CTE.

A signal peptide sequence can also be included in the vector to provide for secretion of a polypeptide from a mammalian cell. Examples of signal peptides include, but are not limited to, the endogenous signal peptide for HGH and variants thereof; the endogenous signal peptide for interferons and variants thereof, including the signal peptide of type I, II and III interferons and variants thereof; and the endogenous signal peptides for known cytokines and variants thereof, such as the signal peptide of erythropoietin (EPO), insulin, TGF-β1, TNF, IL1-α, and IL1-β, and variants thereof. Typically, the nucleotide sequence of the signal peptide is located immediately upstream of the heterologous sequence (e.g., fused at the 5' of the coding region of the protein of interest) in the vector.

In further examples, the vectors can contain a regulatory sequence that allows, for example, the translation of multiple proteins from a single mRNA. Non-limiting examples of such regulatory sequences include internal ribosome entry site (IRES) and 2A self-processing sequence, such as a 2A peptide site from foot-and-mouth disease virus (F2A sequence).

Host Cells

Also provided herein are host cells comprising a nucleic acid molecule or vector or of the present disclosure. In some instances, the host cells are used to amplify, replicate, package and/or purify a polynucleotide or vector. In other examples, the host cells are used to express a heterologous sequence, such as one packaged within AAV vector. Exemplary host cells include prokaryotic and eukaryotic cells. In some instances, the host cell is a mammalian host cell. It is well within the skill of a skilled artisan to select an appropriate host cell for the expression, amplification, replication, packaging and/or purification of a polynucleotide, vector or rAAV virion of the present disclosure. Exemplary mammalian host cells include, but are not limited to, HEK-293 cells, HeLa cells, Vero cells, HuH-7 cells, and HepG2 cells.

Compositions and Methods

Also provided are compositions comprising the nucleic acid molecules, polypeptides and/or vectors of the present disclosure. In particular examples, provided are pharmaceutical compositions comprising the recombinant virions disclosed herein and a pharmaceutically acceptable carrier. The compositions can also comprise additional ingredients such as diluents, stabilizers, excipients, and adjuvants.

The carriers, diluents and adjuvants can include buffers such as phosphate, citrate, or other organic acids; antioxidants such as ascorbic acid; low molecular weight polypeptides (e.g., less than about 10 residues); proteins such as serum albumin, gelatin or immunoglobulins; hydrophilic polymers such as polyvinylpyrrolidone; amino acids such as glycine, glutamine, asparagine, arginine, or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as Tween™, Pluronics™ or polyethylene glycol (PEG). In some embodiments, the physiologically acceptable carrier is an aqueous pH buffered solution.

The AAV vectors of the present disclosure, and compositions containing the AAV vectors, may be used in methods for the introduction of a heterologous sequence into a host cell. Such methods involve contacting the host cell with the AAV vector. This may be performed in vitro, ex vivo or in vivo.

When the methods are performed ex vivo or in vivo, typically the introduction of the heterologous sequence into the host cell is for therapeutic purposes, whereby expression of the heterologous sequence results in the treatment of a disease or condition. Thus, the AAV vectors disclosed herein can be administered to a subject (e.g., a human) in need thereof, such as subject with a disease or condition amendable to treatment with a protein, peptide or polynucleotide encoded by a heterologous sequence described herein.

Titers of AAV vectors to be administered to a subject will vary depending on, for example, the particular recombinant virus, the disease or disorder to be treated, the mode of administration, the treatment goal, the individual to be treated, and the cell type(s) being targeted, and can be determined by methods well known to those skilled in the art. Although the exact dosage will be determined on an individual basis, in most cases, typically, recombinant viruses of the present disclosure can be administered to a subject at a dose of between $1 \times 10^{10}$ genome copies of the recombinant virus per kg of the subject and $1 \times 10^{14}$ genome copies per kg.

The route of the administration is not particularly limited. For example, a therapeutically effective amount of the AAV vector can be administered to the subject by via, for example, intramuscular, intravaginal, intravenous, intraperitoneal, subcutaneous, epicutaneous, intradermal, rectal, intraocular, pulmonary, intracranial, intraosseous, oral, buccal, or nasal routes. The AAV vector can be administered as a single dose or multiple doses, and at varying intervals.

Capsid Diversification

The nucleic acid molecules of the present disclosure that encode the capsid polypeptides may be used in techniques for capsid diversification, which produce rAAV with chimeric capsids that contain regions or domains of capsids from multiple serotypes. Exemplary of such techniques are capsid shuffling techniques, which utilize multiple capsid genes that are then "shuffled" to generate a chimeric capsid gene, typically a library of chimeric capsid genes. These can then be used to produce rAAV comprising chimeric capsid proteins. Generally, a library of rAAV is produced, which is then screened to identify capsids and rAAV having desirable traits, such as reduced immunogenicity, reduced cross-reactivity and altered or improved cell tropism. The nucleic acid molecules of the present disclosure can therefore be used in such methods to produce a chimeric capsid and rAAV comprising the chimeric capsid. Accordingly, the present disclosure is also directed to methods for producing chimeric capsid genes, methods for producing vectors comprising the genes, methods for producing chimeric capsid polypeptides encoded by the genes and methods for producing rAAV comprising the chimeric capsids. Also contemplated are capsid genes, capsid gene libraries, vectors, vector libraries, capsid polypeptides, capsid polypeptide libraries, rAAV and rAAV libraries produced by these methods.

Various capsid shuffling methods have been described in the art. These include "DNA family shuffling" techniques, which have been used to generate diverse libraries of many types of proteins. DNA family shuffling involves in vitro recombination of related genes (in this instance, capsid genes) with >50% homology. The genes are first enzymatically fragmented and then reassembled based on partial homology, resulting in libraries of chimeric genes. DNA family shuffling techniques to produce chimeric capsids have been well described, such as by Grimm et al. (J. Virol. 2008. 82: 5887-5911), Koerber et al. (Mol Ther. 2008. 16: 1703-1709), and Li et al. (Mol Ther. 2008. 16: 1252-1260) in U.S. Pat. Nos. 7,588,772 and 9,169,299, and are well known to those of skill in the art. Such methods can be performed using the nucleic acids provided herein that encode a capsid polypeptide of the disclosure.

Briefly, the methods can include providing two or more different capsid genes from two or more AAV serotypes, wherein one capsid gene encodes a capsid polypeptide of the present disclosure; enzymatically digesting the capsid genes, such as with DNase I, to produce fragments; and reassembling the fragments into chimeric capsid genes which produces a library of chimeric plasmid genes. Reassembly of the gene fragments can be performed by PCR. Because of the related nature of the different capsid genes, the gene fragments have overlapping regions of homology that allow the fragments to self prime in the absence of additional primer in the PCR. Thus, non-primer driven PCR can be used to assemble the fragments into chimeric capsid genes that contain capsid regions from multiple AAV serotypes. In some embodiments, primer-driven PCR is then also used to further amplify the chimeric capsid genes. The method can therefore produce a chimeric capsid gene encoding a chimeric capsid polypeptide that contains a fragment, region or domain of a capsid polypeptide of the present disclosure. The fragment, region or domain may comprise, for example, one or more of the variable regions (VR), including VR-I, VR-II, VR-III, VR-IV, VR-V, VR-VI, VR-VII, VR-VIII and/or VR-IX, and/or the PLA2 domain, as described above. Typically, a library of chimeric capsid genes is produced.

The chimeric genes are then typically introduced into vectors. The vectors may be, for example, basic plasmids that facilitate subsequent cloning, amplification, replication and/or expression. Where a library of chimeric capsid genes is used, a vector library (e.g. a library of plasmid comprising chimeric capsid genes) is produced. These in turn can be used to produce AAV libraries comprising chimeric capsid proteins, which are encoded by the chimeric capsid genes.

Methods of producing AAV vector libraries (replication-deficient) and AAV libraries (replication competent) are well known in the art. For example, and in brief, to produce an AAV library, chimeric capsid genes in a capsid gene library are typically cloned into a shuttle plasmid based on wild-type AAV to produce a construct or plasmid library. Plasmids and methods for producing these construct libraries are well known to those skilled in the art. The construct library is subsequently packaged to produce an AAV library. In contrast to recombinant AAV vector libraries, the replication competent AAV libraries contain AAV with all the same elements as wild-type virus, i.e. 5' ITR, 3' ITR, cap gene (in this case a chimeric cap gene) and rep gene (compared to AAV vector libraries which contain rAAV that do not contain rep and cap genes). As a result, these libraries are viral libraries and not vector libraries. The AAV in the library can then be titrated and used in in vitro or in vivo models to select for chimeric capsids with desirable properties, which can then be vectorized. Methods for vectorizing AAV (i.e. producing replication-deficient AAV vectors) are well known in the art and described briefly above.

Other Uses

The mAAV sequences described herein can also be used for other purposes. For example, the mAAV nucleic acid sequences, including those set forth in SEQ ID NOs:1, 4, 8 and 9 can be used to detect other AAV sequences. This detection of other AAV sequences can be achieved using any of the methods known the art, including, but not limited to, the use of polymerase chain reaction (PCR) using AAV-specific primers, or the use of detectable AAV-specific oligonucleotide probes. For example, DNA isolated samples from various animals can be screened for the presence of AAV sequences by PCR using PCR primers (i.e. a 5' primer and a 3' primer) designed using the mAAV sequences of the present disclosure. The primers have a sequence sufficiently complementary to, or the same as, a sequence flanking a target region within the sequences set forth in SEQ ID NOs: 1, 4, 8 and 9 such that the primers hybridize to a nucleic molecule containing the AAV target region under high, medium or low stringency conditions. In some examples, the primers have 80%, 81%, 82%, 83%, 84%, 85%, 86%, 87%, 88%, 89%, 90%, 91%, 92%, 93%, 94%, 95%, 96%, 97%, 98% or more sequence identity to a sequence within the sequences set forth in SEQ ID NOs:1, 4, 8 and 9 or a reverse, complementary sequence thereto, i.e. the sequences flanking the target region have 80%, 81%, 82%, 83%, 84%, 85%, 86%, 87%, 88%, 89%, 90%, 91%, 92%, 93%, 94%, 95%, 96%, 97%, 98% or more sequence identity to a sequence within the sequences set forth in SEQ ID NOs:1, 4, 8 and 9 or a reverse, complementary sequence thereto. Typically, the primers are at least 15, 16, 17, 18, 19, 20, 21, 22, 23, 24, 25, 26, 27, 28, 29, or 30 nucleotides in length. Generally, the primers are from 15 to 40 or from 15 to 30 nucleotides in length. These primers can therefore be used to amplify the corresponding target region in another AAV sequence present in the sample, i.e. used to generate amplicons containing the target region. Generally, the amplicons are between 50 and 500 nucleic acids in length, such as about 50, 60, 70, 80, 90, 100, 120, 140, 160, 180, 200, 220, 240, 260, 280, 300, 320, 340, 360, 380, 400, 420, 440, 460, 480 or 500 nucleic acids in length. In some embodiments, sequencing of the amplicons is also performed.

Thus, the present disclosure also provides a method for detecting AAV nucleotide sequences in a sample, comprising performing PCR on the DNA under conditions that allow for specific amplification of a target AAV region with a pair of PCR primers consisting of a first PCR primer (e.g. a 5' primer) and a second PCR primer (e.g. a 3' primer) that are designed to amplify the target AAV region, wherein the first PCR primer and the second PCR primer hybridize to and form a duplex with AAV sequences that flank the target AAV region, wherein the target region corresponds to a region within the sequences set forth in SEQ ID NOs:3-20, 22, 29, 32, 33, 36 or 37 and wherein the presence of amplicons containing the target region and resulting from the PCR indicates that AAV nucleotide sequences have been detected in the DNA.

In order that the invention may be readily understood and put into practical effect, particular preferred embodiments will now be described by way of the following non-limiting examples.

The reference in this specification to any prior publication (or information derived from it), or to any matter which is known, is not, and should not be taken as an acknowledgment or admission or any form of suggestion that that prior publication (or information derived from it) or known matter forms part of the common general knowledge in the field of endeavour to which this specification relates.

EXAMPLES

Example 1. Identification of Marsupial AAV Sequences

A QIAamp DNA Stool Mini Kit (Qiagen) was used to extract DNA from marsupial faecal samples, including *Macropus giganteus, Macropus rufogriseus, Thylogale thetis, Wallabia bicolor, Trichosurus vulpecula, Vombatus ursinus* and *Phascolarctos cinereus*.

Initial screening of faecal DNA was by use of two PCR primers designed to amplify from all known AAVs. The forward primer (AAV univ_lin: 5' AATGATACGGCGA CCACCGAGATCTCCNTNYTAYGGNTGYGTNAAY-TGGACYAAYSARAAYTTYCC 3') (SEQ ID NO: 10) hybridizes to a highly conserved region of rep, and the reverse primers (AAV2_3085_rev+N: 5' CAAGCAGAA-GACGGCATACGAGCCCCCARTNGTTRTTR ATRAG-NCKYTGCCAGTC 3' (SEQ ID NO: 11); and "AAV2_3095_rev+N: 5' CAAGCAGAAGACGGCAT-ACGAGCNANNCCCCARTNGTTRTTRATRAGNC 3') (SEQ ID NO: 12) hybridize to a highly conserved region of cap. The primers were synthesized with "hand-mixed" N positions to ensure perfectly equimolar contributions of A, C, G and T.

These primer combinations yielded an amplicon of approximately 2.6 kb. The sequences of the amplicons were iteratively extended by the use of primers amplifying out of the known portion and microhomology primers. The latter consisted of short regions of AAV microhomologies that were identified in AAV alignments, followed by degenerate positions and specified tail sequences that could be used for reamplification. Typically, the target-specific amplicons generated using the microhomology PCR could not be visualised on agarose gels, necessitating detection by Southern blot using probes homologous to the known sequence portion of amplicons. That facilitated identification of the exact size of the desired amplicons, which were then excised based on their size from the unused PCR volume.

Fifty six amplicons were obtained, sequenced and used to generate a consensus mAAV sequence (SEQ ID NO:1). The consensus mAAV cap sequence within this is set forth in SEQ ID NO:2, and encodes a mAAV capsid protein having the sequence set forth in SEQ ID NO:3. From alignment with other AAV capsid sequences, the consensus mAAV cap lacked 30 nucleotides at 3' end, i.e. 10 amino acids at the C terminus of the consensus mAAV capsid protein. The C terminal 10 amino acids were then deduced by alignment with other AAVs to generate the full length VP1 protein set forth in SEQ ID NO:5 (encoded by the polynucleotide set forth in SEQ ID NO:4). Subsequently, and do as to confirm that the deduced C terminus was reasonable, a library of the mAAV capsid sequences that represented all possible permutations at the last 10 amino acids was also generated. Following selection in Tammar wallaby cells, it was observed that 20 out of 24 clones encoded the same last 10 amino acids that were deduced by alignment.

The predicted VP2 and VP3 polypeptides within the full length VP1 protein set forth in SEQ ID NO:5 are set forth in SEQ ID NOs:6 and 7, respectively, and are encoded by the polynucleotides set forth in SEQ ID NOs:8 and 9, respectively.

Example 2. Production of Chimeric AAV with mAAV Capsid

The consensus mAAV capsid sequence (SEQ ID NO:4) was synthesized and provided in a plasmid by genScript. The sequence was digested from the plasmid and inserted into the 388PCR+AAV2 plasmid, which contains AAV2 ITRs and AAV2 rep. Chimeric AAV virus (chimeric mAAV) containing the mAAV capsid and AAV2 ITRs and rep was then produced using Ad5 help and purified with iodixanol gradient using standard protocols. Titration of the virus by qPCR showed that this chimeric mAAV was produced at concentrations of $3.11 \times 10^{13}$ vg/mL.

Figure 2:
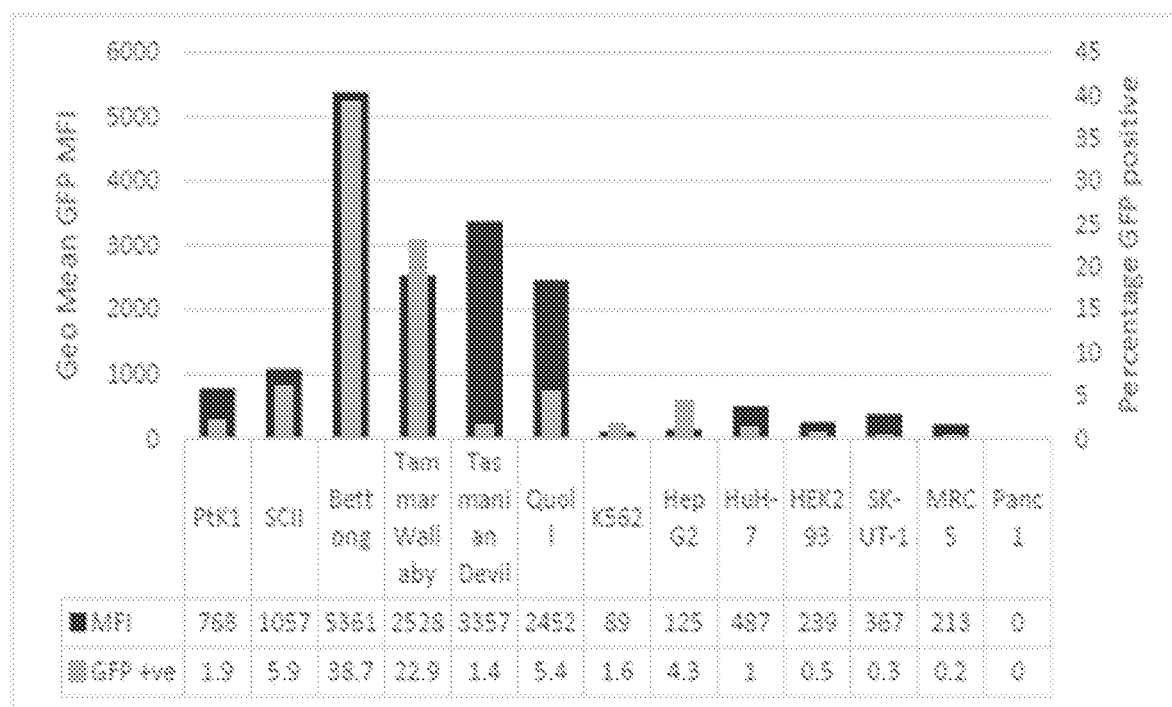
FIG. 2 shows the results of FACS analysis of marsupial and human cells transduced with 2/mAAV.CB7.GFP. Both the geometric mean of the MFI (mean fluorescent intensity) and the percentage of GFP positive cells are shown.

Gel electrophoresis was performed on the chimeric mAAV, alongside AAV2, under reducing conditions. Following electrophoresis, the gel was stained using the SilverQuest™ Silver Staining Kit (Invitrogen) essentially according to manufacturer's instructions. As shown in FIG. 2, each of the VP1, VP2 and VP3 proteins were observed to be present in the mAAV capsid (FIG. 1). Table 2 provides the predicted molecular weight of these proteins.

TABLE 2

| Predicted MW of capsid proteins (kDa) | | |
| --- | --- | --- |
| | mAAV | AAV2 |
| VP1 | 81.7 | 81.9 |
| VP2 | 65.3 | 66.6 |
| VP3 | 59.5 | 60.0 |

Example 3. Production of Chimeric Vectors with mAAV Capsids

The mAAV capsid sequence was cloned into the pRep2 backbone (a plasmid containing the AAV2 rep without ITRs and thus not able to form viral particles on its own), yielding pRep2_CHmAAV. To produce AAV vector, pRep2_CHmAAV was used to package eGFP under the transcriptional control of either the CB7 or the LSP1 promoter in HEK293D cells. The CB7.GFP plasmid contains AAV2 ITRs flanking the CB7 promoter (Chandler and Vendeitti (2010) Mol Ther. 18(1): 11-6) operably linked to an eGFP gene, while the LSP1.GFP plasmid contains AAV2 ITRs flanking the LSP1 promoter (Cunningham et al. (2008) Mol Ther. 16(6): 1081-8) operably linked to an eGFP gene.

Briefly, HEK293D cells were grown in tissue culture dishes at 80% confluency and were transfected with 25 µg DNA/dish: 5 µg pRep2_CHmAAV plasmid, 5 µg CB7.GFP or LSP1.GFP plasmid, and 15 µg helper plasmid) using calcium phosphate transfection. Cells were harvested about 48-60 hours following transfection and the washed cell suspension was freeze-thawed 3-4 time in a dry ice/100% ethanol bath (approximately 15-20 minutes for each freeze and for each thaw approximately 2 hr 20 min). The samples were vortexed between each freeze/thaw. The sample was centrifuges at 4000 rpm (2600× g) for 15 min and the supernatant was collected. Benzonase was added at 50 units/mL and the sample incubated at 37° C. for 30 min before being centrifuged at 4000 rpm for 10 min. The supernatant was collected and ice-cold saturated $(NH_4)_2SO_4$ (pH 7.0) was added at ⅓ the original volume (e.g. 10 mL for 30 mL supernatant) and incubated on ice for 10 min. The samples was again centrifuged at 4000 rpm for 15 min and the supernatant collected before ice-cold saturated $(NH_4)_2SO_4$ (pH 7.0) was added at ⅔ the original volume. The sample was incubated on ice for 20 min and centrifuged at 12000× g for 15 min, before the AAV were purified using a CsCl gradient. The purified AAV was dialysed with PBS twice then PBS with 5% glycerol. AAV was then concentrated using Vivaspin®20 100,000 MWCO centrifugal concentrators by centrifugation at 4000× g at 4° C.

The resulting chimeric vectors contained mAAV capsids encapsidating a vector genome comprising AAV2 ITRs flanking either the CB7 promoter operably linked to an eGFP gene (2/mAAV.CB7.GFP), or the LSP1 promoter operably linked to an eGFP gene (2/mAAV.LSP1.GFP). As vectors contained eGFP, they were tittered using a Quantifast Sybr Green Kit (Qiagen) with GFP-specific primers essentially according to manufacturer's instructions.

TABLE 3

Vector titres

| Vector name | Vector/μl | Vector/mL | Concentrated volume (μl) | Total vector genomes | Vector/dish |
|---|---|---|---|---|---|
| 2/mAAV.CB7.GFP | 4.E+09 | 4.08E+12 | 690 | 2.81E+12 | 4.69E+10 |
| 2/mAAV.LSP1.GFP | 6.24E+11 | 6.24E+14 | 500 | 3.12E+14 | 5.20E+12 |

Example 4. Transduction of Marsupial Cells with mAAV Vectors

A range of marsupial and human cells were transduced with 2/mAAV.CB7.GFP. These included human cells K562, HepG2, HUH7, HEK293, SK-UT-1, MRCS and Panc1, and marsupial cells PtK1, SCII, Bettong (primary cell line) and Tammar Wallaby (primary cell line). Briefly, cells were seeded at a concentration of $10^5$ cells/well (24 well plate) before being transduced with 3 MOIs of vector: $10^5$, $10^4$ and $10^3$. Cells were transduced overnight with a media change the next day. Three days following transduction, the cells were harvested and washed before being re-suspended in FACS buffer and run on the FACS Canto to detect GFP-positive cells. Both the geometric mean of the MFI (mean fluorescent intensity) and the percentage of GFP positive cells were recorded.

As shown in FIG. 2, which depicts transduction using $10^5$ vector genomes/cell, the mAAV vector was more efficient at transducing marsupial cells than human cells.

Example 5. Transduction of Mouse Liver with mAAV Vector

To assess if the mAAV capsid showed tropism for any mouse tissues, both of the 2/mAAV.CB7.GFP and 2/mAAV.LSP1.GFP vectors were injected into mice. Briefly, male 8-10 week old C57B16 mice were injected with 2/mAAV.CB7.GFP ($1\times10^{11}$ vg/mouse) and 2/mAAV.LSP1.GFP ($0.5\times10^{11}$ vg/mouse) via intraperitoneal injection. Mice were euthanized after 2 weeks, and the brain, heart, liver, pancreas, spleen, kidney, lung, heart and brain collected for molecular and histological analysis.

Figure 3:
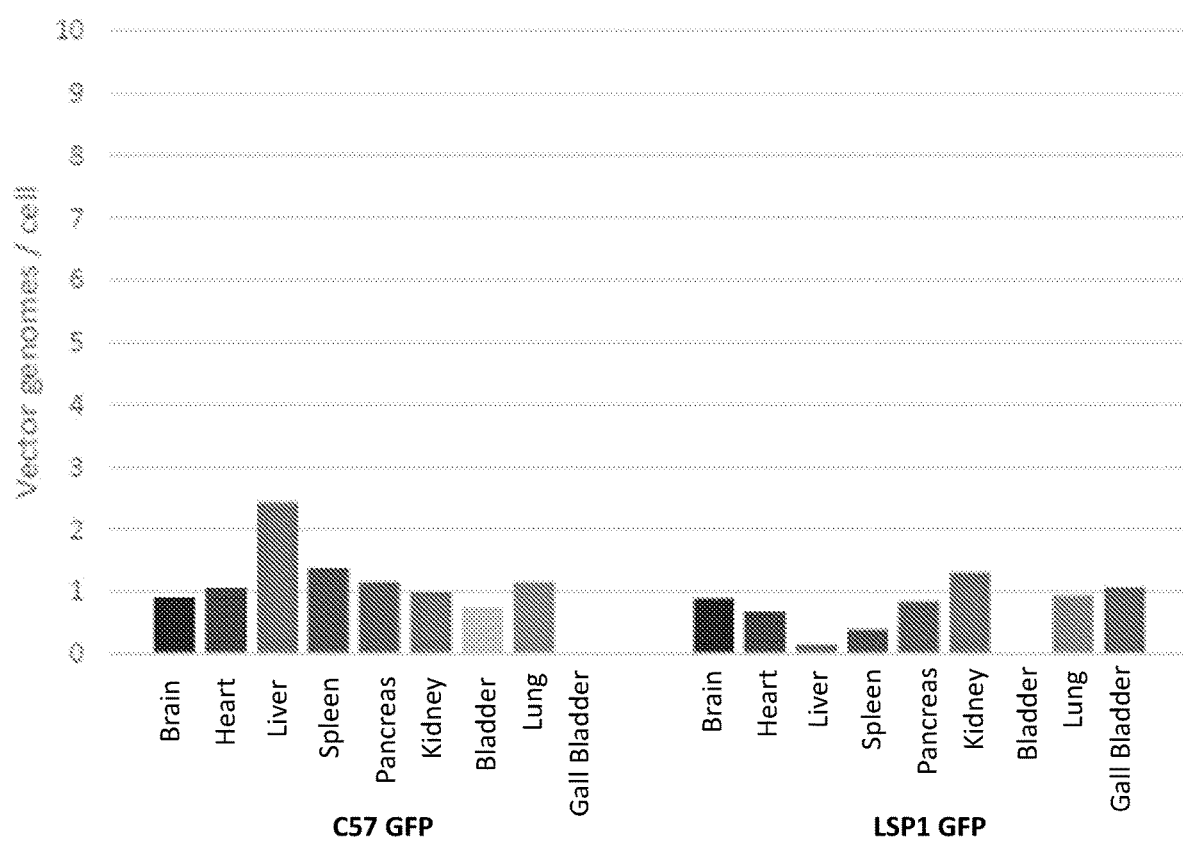
FIG. 3 shows the number of vector genomes per cell in various organs 2 weeks after intraperitoneal injection of C57B16 mice with 2/mAAV.CB7.GFP and 2/mAAV.LSP1.GFP.

DNA was extracted from the tissues and analyzed by GFP qPCR to determine vector copy numbers in each organ. As shown in FIG. 3, vector copy numbers were very low in each organ. Liver samples were also cryosectioned and analyzed for GFP expression, although no GFP positive cells were detected.

Example 6. Shuffled Capsid Library Generation

A shuffled capsid library was generated using the consensus mAAV capsid gene as well as capsid genes from AAV1, AAV2, AAV3, AAV4, AAVS, AAV6, AAV7, AAV8, AAV9, AAV10, AAV11, AAV12 and an ancient AAV-derived endogenous viral element found within the genome of multiple marsupial species (AAV-EVE1, described in WO2017192699). AAV libraries were generated as described previously (Lisowski et al. (2014) Nature 506, 382-386) with minor modifications. The AAV capsid genes from wild-type serotypes AAV1 (NC_002077.1), AAV2 (NC_001401.2), AAV3 (AF028705.1), AAV4 (NC_001829.1), AAVS (amplified from pXR5 plasmid, which differs at two positions, A123T and A234T, from NC_006152.1), AAV6 (AF028704.1), AAV7 (AF513851.1), AAV8 (AF513852.1), AAV9 (AY530579.1, AAV10 (AY631965.1), AAV11 (AY631966.1), AAV12 (DQ813647.1), AAV-EVE1 (MG657004) and mAAV were cloned into the p-RescueVector (pRV 1-12), a plasmid based on pGEM®-T Easy Vector System (Promega Cat #A1360) modified to harbor Trimethoprim resistance and randomized ends flanking the capsids, for optimal Gibson Assembly (GA) reaction. Individual clones were Sanger sequenced (Garvan Molecular Genetics). Capsid genes were excised using SwaI and NsiI (NEB), mixed at 1:1 molar ratios and digested with 1:10 prediluted DNaseI (NEB Cat #M030S) for 2 to 5 min. The pool of fragments was separated on 1% (w/v) agarose gel and fragments ranging from 200 bp to 1000 bp were recovered with Zymoclean Gel DNA Recovery Kit (Zymogen Cat #D4001T). 500 ng of gel extracted fragments were used in a primer-less PCR reassembly reaction and fully reassembled capsids were amplified in a second PCR with forward and reverse primers binding the capsid gene and carrying overlapping ends to pRVplasmids. Gibson Assembly Reaction (GAR) was performed by mixing equal volume of 2× Gibson Assembly Master Mix (NEB Cat #E2611L) with 1 pmol of PCR amplified and DpnI treated pRV and 1 pmol of the recovered shuffled capsids, at 50° C. for 30 min. DNA was ethanol precipitated, and electroporated into SS320 electro-competent cells (Lucigen Cat #60512-2). Total number of transformants was calculated by preparing and plating five 10-fold serial dilutions from the electroporated cells. The pool of transformants was grown overnight in 250 mL LB media with trimethoprim (10-μg/mL). Total pRV library plasmids were purified with an EndoFree Maxiprep Kit (QIAGEN Cat #12362). N=30 individual clones were picked and Sanger sequenced in order to confirm library variety. pRV based libraries were then digested overnight with SwaI and NsiI and 1.4 μg of insert was ligated at 16° C. with T4 ligase (NEB Cat #M0202) for 16 hours into 1 μg of a replication competent AAV2 based plasmid platform (p-Replication-Competent, p-RC) containing ITR-2 and rep2, and unique SwaI and NsiI flanking a 1-kb randomized stuffer (ITR2-rep2-(SwaI)-stuffer-(NsiI)-ITR2). Ligation reaction was concentrated by ethanol precipitation, electroporated into SS320 electro-competent cells and grown as described before. Total pRC library plasmids were purified with an EndoFree Maxiprep Kit (QIAGEN Cat #12362).

Libraries were also produced as essentially described above but using a codon-optimized consensus mAAV capsid gene, as well as codon-optimized capsid genes from AAV1, AAV2, AAV3, AAV4, AAVS, AAV6, AAV7, AAV8, AAV9, AAV10, AAV11, AAV12 and the ancient AAV-derived endogenous viral element, as described in Cabanes-Crues et al. (unpublished) and Australian provisional patent application no. 2018900609.

Sequence analysis of 40 individual clones from the non-codon-optimized library indicated that the number of parental segments per clone was 14.57±4.71, the number of parental variants contributing was 7.87±1.43, and the average length of donor segments was 140.8 bp. The percentage of shuffled clones in this library containing mAAV sequence was 13.3%. Sequence analysis of 40 individual clones from the codon-optimized library indicated that the number of parental segments per clone was 16.77±3.21, the number of parental variants contributing was 10.17±1.57, and the average length of donor segments was 126 bp. The percentage of shuffled clones in this library containing mAAV sequence was 63.3%.

The invention claimed is:

1. An isolated capsid polypeptide, comprising a sequence of amino acids having at least 95% sequence identity to the sequence set forth in SEQ ID NO:7.

2. An isolated capsid polypeptide, comprising a sequence of amino acids having at least 95% sequence identity to the sequence set forth in SEQ ID NO:5.

3. The isolated capsid polypeptide of claim 1, comprising:
  (a) a region selected from the group consisting of:
    (i) a variable region (VR)-I set forth in amino acid residues 263-271 of SEQ ID NO:5;
    (ii) a VR-II set forth in amino acid residues 227-231 of SEQ ID NO:5;
    (iii) a VR-III set forth in amino acid residues 381-389 of SEQ ID NO:5,
    (iv) a VR-IV set forth in amino acid residues 449-462 of SEQ ID NO:5;
    (v) a VR-V set forth in amino acid residues 481-496 of SEQ ID NO:5;
    (vi) a VR-VI set forth in amino acid residues 517-535 of SEQ ID NO: 5;
    (vii) a VR-VII set forth in amino acid residues 538-556 of SEQ ID NO: 5;
    (viii) a VR-VIII set forth in amino acid residues 579-595 of SEQ ID NO: 5;
    (ix) and VR-IX set forth in amino acid residues 704-711 of SEQ ID NO: 5;
  (b) the sequence set forth in SEQ ID NO:7;
  (c) the sequence set forth in SEQ ID NO:6; or
  (d) the sequence set forth in SEQ ID NO:5.

4. An AAV vector, comprising the capsid polypeptide of claim 1.

5. The AAV vector of claim 4, further comprising a heterologous sequence.

6. A nucleic acid molecule encoding the capsid polypeptide of claim 1.

7. A vector comprising the nucleic acid molecule of claim 6.

8. The vector of claim 7, wherein the vector is selected from among a plasmid, cosmid, phage and transposon.

9. A method for introducing a heterologous sequence into a host cell, comprising contacting a host cell with the AAV vector of claim 5.

10. A method for producing an AAV vector, comprising:
  (a) introducing into a cell a nucleic acid molecule encoding the capsid polypeptide of claim 1, an AAV rep gene, a heterologous sequence flanked by inverted terminal repeats, and helper functions for generating a productive AAV infection; and
  (b) allowing assembly of an AAV vector comprising a capsid comprising the capsid (b) polypeptide of claim 1, wherein the capsid encapsidates the heterologous sequence.

\* \* \* \* \*